(12) United States Patent
Vigh et al.

(10) Patent No.: US 6,511,850 B1
(45) Date of Patent: Jan. 28, 2003

(54) PNEUMATIC NEBULIZING INTERFACE TO CONVERT AN ANALYTE-CONTAINING FLUID STREAM INTO AN AEROSOL, METHOD FOR USING SAME AND INSTRUMENTS INCLUDING SAME

(75) Inventors: Gyula Vigh, Magnolia, TX (US); Alex D. Sokolowski, Albany, NY (US)

(73) Assignee: The Texas A&M University System, College Station, TX (US)

( * ) Notice: Subject to any disclaimer, the term of this patent is extended or adjusted under 35 U.S.C. 154(b) by 317 days.

(21) Appl. No.: 09/614,368

(22) Filed: Jul. 12, 2000

Related U.S. Application Data

(60) Provisional application No. 60/143,604, filed on Jul. 13, 1999.

(51) Int. Cl.[7] ............................. H01J 49/04; B05B 7/30
(52) U.S. Cl. ...................... 436/127; 239/341; 239/348; 250/288; 261/78.2; 422/52; 422/70; 422/78; 422/80; 422/81; 422/82.01; 422/82.05; 422/54; 436/36; 436/52; 436/54; 436/153; 436/160; 436/161; 436/172; 436/173; 436/174; 204/452
(58) Field of Search ............................. 422/52, 70, 78, 422/54, 80, 81, 82.01, 82.05; 436/36, 52, 54, 127, 155, 160, 149, 150, 153, 161, 172, 173, 174; 239/290, 338, 340, 341, 347, 348, 365–372; 261/78.1, 78.2, 76; 250/288; 204/452

(56) References Cited

U.S. PATENT DOCUMENTS

| | | | |
|---|---|---|---|
| 3,298,785 A | 1/1967 | Reul ............................ 23/230 | |
| 3,963,182 A | * 6/1976 | Rulseh | |
| 4,066,409 A | 1/1978 | Fine ......................... 23/230 PC | |
| 4,582,654 A | 4/1986 | Karnicky et al. ............. 261/81 | |
| 4,636,364 A | * 1/1987 | Geyer et al. | |
| 4,843,016 A | 6/1989 | Fine ............................ 436/106 | |
| 4,904,606 A | 2/1990 | Forster et al. ............... 436/177 | |
| 4,914,037 A | 4/1990 | Forster et al. ............... 436/106 | |
| 4,916,077 A | 4/1990 | Forster et al. | |

(List continued on next page.)

FOREIGN PATENT DOCUMENTS

| | | |
|---|---|---|
| FR | WO 87/07721 | 12/1987 |
| GB | 1069267 | 5/1967 |
| WO | WO 98/38507 | 2/1997 |
| WO | WO 01/03848 A1 | 1/2001 |

OTHER PUBLICATIONS

Proceedings of the Sixth International Conference on Liquid Atomization and Spray Systems Jul. 18–22, 1994, Palais des Congres, Rouen, France, Edited by Andrew J. Yule and Christophe Dumouchei, Begell House, Inc. New York Spray Characterization in a Confined Flow by Trichet and Lavergne.

(List continued on next page.)

*Primary Examiner*—Jan Ludlow
(74) *Attorney, Agent, or Firm*—Robert W. Strozier

(57) ABSTRACT

A self-adjusting, free-flowing pneumatic nebulizer interface is described for coupling fluid phase separation apparatus such as capillary electrophoresis apparatus or fluid-phase analyte delivery apparatus such as flow-injection analysis apparatus to gas phase, post-separation detection apparatus such as mass spectrometers, chemiluminescence detectors, or other similar gas phase detection apparatus. The interface combines the analytes with only the needed amount of sheath fluid to produce a combined flow whose magnitude automatically matches the self-aspiration rate of the pneumatic nebulizer interface, and which is combined with a gas flow to produce an aerosol. The resulting aerosol can then be either deposited directly on a surface, forwarded directly to a detection system or forwarded first to a conversion apparatus such as an oxidizer and the oxidized sample components are then forwarded to a detector.

26 Claims, 13 Drawing Sheets

U.S. PATENT DOCUMENTS

| | | | |
|---|---|---|---|
| 4,950,456 A | | 8/1990 | Forster et al. .................. 422/80 |
| 5,175,433 A | * | 12/1992 | Browner et al. |
| 5,393,975 A | | 2/1995 | Hail et al. .................. 250/288 |
| 5,738,281 A | * | 4/1998 | Zurecki et al. |
| 5,884,846 A | | 3/1999 | Tan ............................ 239/338 |

OTHER PUBLICATIONS

PD. vol. 57 Emerging Energy Technology 1994, ASME 1994, Parvez and Gollahalll. An Experimental Study of the Lift–Off Characteristics of a Liquid Spray Flame. pp77–83. No Emission of Lean Premixed–Prevaporized Combustion for Liquid Fuels. Narato and Kobayashi et. al. Hitachi Seisakusho.

P. Roth and R. Shamekhi. Waste Water Combustion in a Confined Swirl Flame. Chemical Engineering Science. vol. 38, No. 7, pp. 1101–1106, 1983.

Fourteenth Symposium (International) on Combustion–.Pennsylvania State University, University Park, Pennsylvania. Aug. 20–25, 1972. Organized by the Combustion Institue. Appleton, JP and Heywood JB: The Effects of Imperfect Fuel—Air Mixing in a Burner on No Formation From Nitroger in the Air and the Fuel., pp. 777–786.

Lord. G.A. Tapers and restrictors for capillary electrochromatography and capillary electrochromatography–mass spectrometry. Journal of Chromatography A 768 (1997) 9–16.

* cited by examiner

PNEUMATIC NEBULIZING INTERFACE TO CONVERT AN ANALYTE-CONTAINING FLUID STREAM INTO AN AEROSOL, METHOD FOR USING SAME AND INSTRUMENTS INCLUDING SAME

This application claims provisional priority to U.S. Provisional Patent Application Ser. No. 60/143,604 filed Jul. 13, 1999.

BACKGROUND OF THE INVENTION

1. Field of the Invention

This invention relates to a pneumatic nebulizing interface designed to convert an analyte-containing fluid stream into an aerosol without causing undesirable, excessive broadening and/or mixing of analyte bands. The interface can be used to supply a sample aerosol to any downstream apparatus including any detection apparatus, reaction apparatus, deposition apparatus, collection apparatus or any combination of these apparatus.

More particularly, the present invention relates to a pneumatic nebulizing interface designed to convert an analyte-containing fluid stream into an aerosol for subsequent reaction, deposition, collection or detection. In the interface, an aerosol is formed from the analyte-containing fluid stream, a sheath fluid and a nebulizing gas. The interface insures that the combined flow rate of the analyte-containing fluid stream and the sheath fluid always substantially exactly matches the self-aspiration rate of the pneumatic nebulizer. The interface maintains the matched combined flow rate without substantially altering the original feed rate of the analyte-containing fluid stream, by automatically self-adjusting the feed rate of the sheath fluid. Thus, neither suction nor back pressure act on the analyte-containing fluid stream and additional broadening and/or mixing of analyte bands in the fluid stream is avoided or minimized during the nebulization process. The present invention also relates to methods for making and using the pneumatic nebulization interface. Furthermore, the present invention also relates to analytical systems which include a fluid phase analyte separation sub-system or analyte delivery sub-system, the interface subsystem and a detection subsystem.

2. Description of Related Art

The currently known pneumatic nebulizer systems suffer from certain disadvantages that hinder their use in high-performance, fluid phase separation systems. The Venturi effect, which forms the basis of operation of pneumatic nebulizers, exerts suction upon the nebulized analyte-containing fluid stream and causes additional dispersion and/or mixing of the analyte bands in the fluid stream Thus, there is a need in the art for a pneumatic nebulizer interface to be used with fluid phase separation techniques or fluid phase analyte delivery techniques to convert an analyte-containing fluid stream into an aerosol such that the interface does not substantially adversely affect the width of the analyte bands in the fluid stream and is capable of substantially self-adjusting the combined flow rate of the analyte-containing fluid stream and a sheath flow stream to the natural self-aspiration rate of the nebulizer without substantially changing the original flow rate of the analyte-containing fluid stream.

SUMMARY OF THE INVENTION

This invention provides an interface to convert an analyte-containing fluid stream into an aerosol. The interface includes an analyte-containing fluid stream inlet, a sheath fluid inlet, a sheath fluid overflow outlet, a gas inlet, a nebulizing nozzle and an aerosol outlet. The analyte-containing fluid stream and the sheath fluid are supplied such that their combined flow rate through the nebulizing nozzle self-adjustingly substantially matches the natural self-aspiration rate of the nebulizing nozzle and does not cause substantial flow rate change and accompanying band width increase in the analyte-containing fluid stream.

The present invention provides a self-adjusting nebulizer apparatus including a first fluid inlet having a first flow resistance and supporting a first fluid flow, a second fluid inlet having a second flow resistance and supporting a second fluid flow, a nebulizing gas inlet supporting a gas flow; and an orifice, where the first fluid inlet, the second fluid inlet and the gas inlet terminate at or near the orifice, the second flow resistance is substantially negligible with respect to the first flow resistance and the first flow and the second flow combine to form a combined fluid flow having a rate that substantially matches the self-aspiration rate of the apparatus without producing substantial back pressure or suction which results in additional laminar flow-induced band dispersion or broadening in the first fluid inlet and the combined flow and gas flow combine to form an aerosol.

The present invention provides a self-adjusting nebulizer apparatus including a sample inlet having a first flow resistance and supporting a sample flow where the sample flow includes an analyte, a sheath fluid inlet having a second flow resistance and supporting a sheath fluid flow, a nebulizing gas inlet supporting a gas flow and an orifice through which the sample flow, the sheath flow and the gas flow exit to form an aerosol, where the sample inlet, the sheath fluid inlet and the gas inlet terminate at or near the orifice, the second flow resistance is substantially negligible with respect to the first flow resistance and the first flow and the second flow combine to form a combined fluid flow having a rate that substantially matches the self-aspiration rate of the apparatus without producing substantial back pressure or suction which results in additional laminar flow-induced band dispersion or broadening in the first fluid inlet.

The present invention provides a self-adjusting nebulizer apparatus including a first fluid inlet having a first resistance to fluid flow and supporting a first fluid flow, a second fluid inlet having a second resistance to fluid flow and supporting a second fluid flow, a nebulizer nozzle downstream of the first inlet and second fluid inlet, a gap connecting the first fluid inlet, the second fluid inlet and the nebulizer nozzle, and a gas inlet tube having an orifice at its distal end, where (1) the second resistance is substantially negligible with respect to the first resistance, (2) the first flow and the second flow combine in the gap to form a combined fluid flow having a rate that substantially matches the self-aspiration rate of the apparatus without producing substantial back pressure or suction which results in additional laminar flow-induced band dispersion or broadening in the first fluid inlet, and (3) the gas and combined fluid flow form an aerosol upon exiting the orifice.

The present invention provides a self-adjusting nebulizer apparatus including a first member including a distal end and having a first resistance to fluid flow and supporting a first fluid flow, a nebulizer nozzle including a proximal end and a distal end, a gap separating the distal end of the first member from the proximal end of the nozzle, a second member having a second resistance to fluid flow and supports a second fluid flow and including an inlet and an outlet associated with the gap, and a third member supporting a gas flow and including an orifice at its distal end, where (1) the distal end of the nozzle is located at or near the orifice, (2)

the second resistance is substantially negligible with respect to the first resistance, and (3) the first flow and the second flow combine in the gap to form a combined fluid flow having a rate that substantially matches the self-aspiration rate of the apparatus without producing substantial back pressure or suction on the first member.

This invention also provides an analytical separation and detection system which includes a fluid phase separation subsystem or analyte delivery subsystem, a downstream deposition or detection subsystem and an interface which connects the upstream subsystems to the downstream subsystems.

This invention further provides a apparatus for generating aerosols and includes an analyte-containing fluid stream feed tube or first inner tube and a nebulizer nozzle or second inner tube separated by a liquid gap. The feed tubes or inner tubes and the gap are contained within a first outer tube having an opening at or near the gap through which a sheath fluid can enter the gap. This sub-assembly is contained within a sheath fluid delivery tube which in turn is contained within a gas delivery tube. The analyte-containing fluid stream feed tube has a diameter less than or equal to the diameter of the nebulizing nozzle. The analyte-containing fluid stream feed tube is designed to interface with or be part of a fluid phase separation subsystem or analyte deliver subsystem at its distal end. The nebulizing nozzle is designed to supply the combined flow of the analyte-containing fluid stream and the sheath fluid to an orifice where the combined flow contacts a gas and is converted into an aerosol.

This invention provides an analytical method which includes separating a sample into its components in a fluid phase. The separated analytes in the fluid phase are then forwarded to a pneumatic nebulizer interface designed to automatically adjust the flow rate of the combined analyte-containing fluid stream and the sheath liquid to substantially match the self-aspiration rate of the nebulizing nozzle without substantially altering the flow rate of the analyte-containing fluid stream. The pneumatic nebulizer interface converts the combined flow into an aerosol by contacting it with the nebulizing gas. The aerosol is then forwarded to a detection system where the analytes are detected and quantified. Moreover, the detection system may involve one or more conversion steps before detection and quantification.

This invention provides an interfacing method which includes the step of supplying the analytes in a fluid stream from a fluid phase separation apparatus or analyte delivery apparatus. Next, the analyte-containing fluid stream is introduced into an interface through an analyte-containing fluid stream feed tube. After introduction, a sheath fluid is supplied to the analyte-containing fluid stream through an opening such that substantially no adverse additional band broadening is caused in the analyte-containing fluid stream. The sheath fluid and the analyte-containing fluid streams then are combined in a gap which is located between the analyte-containing fluid stream feed tube and a nebulizing nozzle. The combined flow then exits the nebulizing nozzle in the orifice where the combined fluid flow contacts a gas to form an aerosol.

This invention provides an interfacing method which includes the step of introducing a fluid stream into an interface through a fluid stream feed tube. After introduction, a sheath fluid is supplied to the fluid stream through an opening such that substantially no adverse mixing occurs in the fluid stream. The sheath fluid and the fluid stream then are combined in a gap which is located between the fluid stream feed tube and a nebulizing nozzle. The combined flow then exits the nebulizing nozzle in the orifice where the combined fluid flow contacts a gas to form an aerosol.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
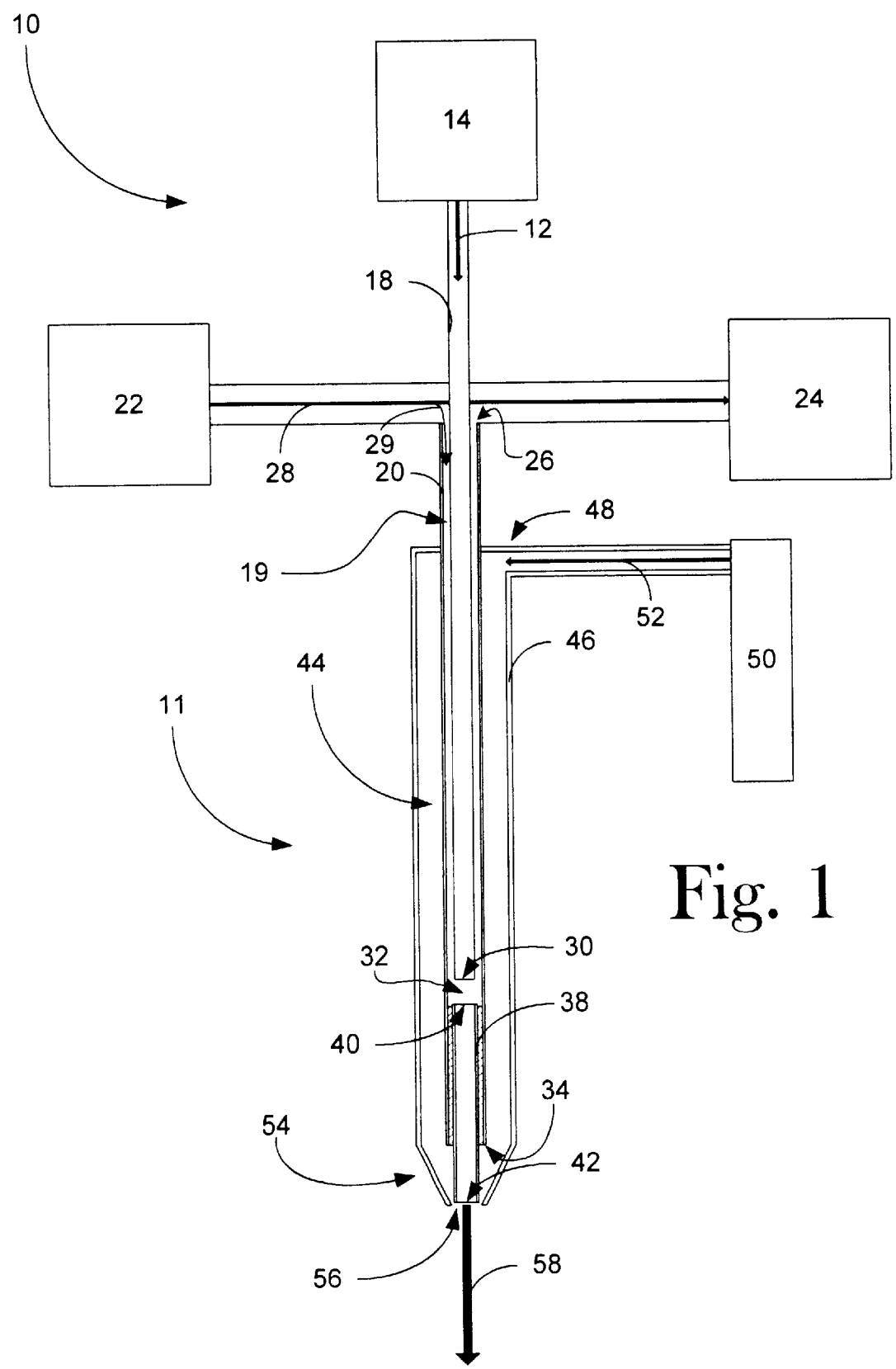
FIGS. 1 and 1A are a cross-sectional and a block diagram of an embodiment of an interface of the present invention.

The inventors have found that an apparatus can be designed that functions as an effective interface capable of converting an analyte-containing fluid stream into an aerosol to be used with further downstream processing apparatus, such as detection apparatus, such that the combined flow rate of the analyte-containing fluid stream and a sheath liquid stream substantially automatically self-adjusts to the self-aspiration flow rate of the nebulizer nozzle without substantially altering the flow rate of the analyte-containing fluid stream and causing undesirable additional broadening or mixing of the analyte bands in the fluid stream.

Four apparatus are broadly envisioned in this invention: (1) an effective interface to convert an analyte-containing fluid stream into an aerosol such that the combined flow rate of the analyte-containing fluid stream and a sheath liquid stream substantially automatically self-adjusts to the self-aspiration flow rate of the nebulizer nozzle without substantially altering the flow rate of the analyte-containing fluid stream and causing undesirable additional broadening or mixing of the analyte bands in the fluid stream; (2) the interface assembly operatively connected to and interposed between a fluid phase separation apparatus or analyte delivery apparatus and a detection apparatus or conversion apparatus; (3) the interface operatively connected to and interposed between a fluid phase separation apparatus or analyte delivery apparatus and an analyte conversion apparatus which is in turn operatively connected to a detection apparatus; and (4) the interface used to convert a fluid stream into an aerosol for deposition on a surface.

The interface can be designed in a number of different formats depending on instrument structure and space limitations. In general, the interface requires an orifice in which gas and liquid combine to form a nebulized output or an aerosol. The liquid is made up of two flows: a sample flow including an analyte and a sheath fluid flow. The two flows combine with the gas to form the aerosol upon exiting the orifice. The sheath flow is self-adjusting so that the combined flow substantially matches the self-aspiration rate of the nebulizer in such a way as to minimize or substantially eliminate back pressure or suction on the sample inlet. The minimization or elimination of back pressure or suction is achieved by insuring that the flow resistance of the sheath fluid supply system is substantially negligible with respect to the flow resistance of the sample inlet and there is an adequate supply of sheath liquid or fluid. Generally, the sheath fluid flow resistance is at least 50 times less than the sample flow resistance, preferably at least 100 times less than the sample flow resistance and particularly at least 500 times less than the sample flow resistance.

Generally, the interface includes an analyte-containing fluid stream supply, a gas supply, a sheath liquid supply, a nebulizer nozzle, and an orifice where the analyte-containing fluid stream, a sheath liquid and a gas combine to form an aerosol.

The interfaces of the present invention are ideally suited for use in combination with high performance separation apparatus such as chromatographic apparatus, electrophoretic apparatus, electrochromatographic apparatus, field flow fractionation apparatus, and with analyte delivery apparatus such as flow injection analysis apparatus or a combination thereof.

If the interface is to be connected to an analyte transformation unit, then the gas supplied to the interface is preferably the gas needed to transform the analyte into a desired transformate. For example, if the analyte is to be oxidized to oxides, the nebulizing gas includes sufficient amounts of an oxidizing agent to transform at least a portion of the analyte to its corresponding oxides. Under such conditions, the aerosol formed is an oxidizer-rich aerosol and if the oxidizer is oxygen, then the aerosol is an oxygen-rich aerosol. The term oxygen-rich means that there is enough oxygen in the resulting aerosol to convert at least a portion of the oxidizable components in the aerosol into their corresponding oxides and at least one of the oxides or class of oxides can be detected after the oxidation step or alternatively, can be subsequently converted to a detectable species. Thus, for example, in an oxygen-rich aerosol, the carbon and nitrogen containing analytes would be converted to oxides of carbon and oxides of nitrogen at concentrations high enough for successful post-combustion detection and analysis. Preferably, the aerosol includes sufficient gas to transform substantially all of the tranformable components into their corresponding transformates. Thus, for oxygen-rich aerosols, the aerosol should contain sufficient, generally an excess of oxygen, to convert substantially all oxidizable components into their corresponding oxides.

Most of the fluid phase separation techniques employ a moving phase, a carrier solution or solvent. If the carrier is non-transformable under the desired transformation conditions, then the required amount of the transforming agent in the nebulizing gas is related only to the amount of the analytes present. However, if the carrier is transformable, then the amount of transforming agent required in the nebulizing gas is related to the total amount of carrier and analytes present. For example, if the transformation is oxidation and the carrier is water, then the amount of oxidizer is proportional only to the amount of analytes in the fluid stream, but if the carrier is combustible, such as methanol, then the amount of oxidizer required in the nebulizing gas is proportional to the combined amounts of analytes and carrier.

When using a combustion zone, the zone is typically contained within a furnace assembly or a torch. The combustion assembly includes an oxidation zone which generally comprises the interior volume of an oxidation or combustion tube. The tube is generally located in a housing designed to maintain the tube at an elevated temperature. Typically, the temperature in the oxidation zone is maintained at a level which insures that, at a given residence time of the aerosol in the oxidization zone, a sufficient amount of the oxygen-rich aerosol can be converted into the corresponding oxides. The temperature of the combustion assembly is generally maintained above about 300° C. with a residence time sufficient to effect the desired degree of combustion. For combustion tubes in furnaces, the combustion assembly is typically maintained at a temperature between about 300° C. and about 1700° C. with a residence time sufficient to effect the desired degree of combustion. For torches, the temperature in the plasma can range to a much higher value.

The combustion assembly converts the oxygen-rich aerosol into combustion gases which include at least one oxide or class of oxides which can be detected in a downstream detection apparatus either directly or after chemical or physical transformation.

Optionally, oxygen-rich aerosols can be mixed with an auxiliary gas or gas mixture either prior to or upon entering the oxidation zone. The auxiliary gas or gas mixture is designed to prevent the aerosol from contacting the surfaces of either the nebulizer or the oxidation zone, control the residence time of the analyte in the oxidation zone, and/or improve the oxidation efficiency.

For oxidatively converted analytes, the downstream detecting apparatus can include any apparatus capable of detecting at least one oxide or class of oxides in the combustion gases. The detection apparatus can be a chemiluminescence detection apparatus, an absorbance detector apparatus, an emission detector apparatus, a fluorescence detection apparatus, a mass spectrometric apparatus or any other detection apparatus used to quantify the amount of a given oxide, or a combination thereof.

Furthermore, the entire apparatus can include additional steps and/or apparatus to convert at least a second oxide or class of oxides into detectable species such as placing a reduction zone between the oxidation zone and the detection apparatus where the reduction zone converts a portion of at least one oxide or class of oxides into species which are detectable in the detection apparatus. This latter configuration is ideally suited for using ozone-induced chemiluminescence to analyze a sample for nitrogen and/or sulfur content or to perform a near simultaneous detection of both the nitrogen and sulfur content of a sample as disclosed in co-pending application Ser. No. 08/760,247, now U.S. Pat. No. 5,916,523, incorporated herein by reference.

For detection of oxidized analyte components, the methods of the present invention broadly incorporates a sample transformation step which involves: (1) forming an oxygen-rich aerosol; (2) reacting the aerosol, at an elevated temperature, to form combustion gases containing at least one detectable oxide or class of oxides; and (3) detecting at least one oxide or class of oxides in the combustion gases in a detection system. The method can also include one or more additional steps subsequent to the reacting and prior to the detecting steps, where the additional step or steps are designed to convert at least one oxide or class of oxides into species which can be detected in a given detection system.

For detection of oxidized analyte components, the present invention is also related to oxygen-rich aerosols including a sample material having at least one sample component entrained in a carrier and an oxidizing gas, where the oxygen-equivalent of the oxidizing gas is greater than the number of oxygen equivalents needed to completely oxidize to the corresponding oxides the sample components and/or the carrier.

The interface of the present invention can also be used to convert the analyte-containing fluid phase stream into an aerosol for subsequent deposition, collection or injection into downstream apparatus such as gas phase separation, reaction or detection apparatus.

Suitable background electrolytes include, without limitation, is a buffer adjusted to a given pH range and can be an aqueous buffer, a mixed solvent buffer system (i.e., a water and a miscible organic solvent) or an organic solvent buffer. Examples of organic solvents are lower alcohols such as methanol, ethanol, isopropanol or the like, acetonitrile, or any other similar organic compound able to dissolve one or more salts to an acceptable solubility. Illustrative examples of such electrolytic buffers include, without limitation, phosphate buffers, citrate buffers, formate buffers, or the like for lower pH conditions (about pH 2 to about pH 5), phosphate buffers using second ionization of phosphate, acetate buffers, or the like for mid range pH conditions (about pH 4 to about pH 8), and borate buffers, carbonate buffers, phosphate buffer using the third phosphate ionization, or the like for high pH conditions (about pH 7 to about pH 12).

Preferred Interface Embodiments

Referring now to FIG. 1, a preferred embodiment of an interface of the present invention generally 10 is shown to include a nebulizer 11, a sample feed or separation apparatus effluent 12 exiting a separation apparatus or analyte delivery apparatus 14. The sample feed 12 enters the interface 10 through a sample inlet 18 where the inlet 18 has an internal diameter $id_1$, a distal end 30 and a first fluid resistance.

A sheath liquid feed tube 20 is shown surrounding a portion 19 of the inlet tube 18. The sheath liquid feed tube 20 is connected at its proximal end 26 to a sheath liquid supply 22 and a sheath liquid overflow 24. The sheath liquid tube 20 is closed at its distal end 34 and has a second fluid resistance where the second fluid resistance is smaller than the first fluid resistance. The sample inlet 18 terminates at its distal end 30 prior to the distal end 34 of the sheath tube 20 and forms a gap 32 between an inlet 40 of a nebulizer nozzle 38 and the outlet 30 of the inlet tube 18. The gap 32 serves as a zone for combining the sample feed or effluent 12 and a portion 29 of a sheath fluid 28. The combined fluid flow (the sum of the sample flow 12 and sheath fluid flow 29) enters the nebulizer nozzle 38 at its inlet 40 and exits at its outlet 42. The nebulizer nozzle 38 has an internal diameter, $id_2$. The length of the nebulizer nozzle 38 is minimized in order to reduce the extent of any flow-induced band broadening in the fluid phase. Generally, the length of the nebulizer nozzle 38 is less than about 20 mm, preferably, less than about 10 mm, particularly, less than about 6 mm and especially less than about 4 mm. Although $id_1$, and $id_2$ can be of any size, the preferred values of these two diameters are where $id_2$ is equal to or greater than $id_1$, particularly, $id_2$ is greater than $id_1$. Generally, $id_1$ and $id_2$ are between about 200 µm and about 1 µm, preferably, between about 150 µm and about 1 µm, and particularly, between about 100 µm and about 5 µm. Of course, as sizes reduce, even smaller id tubes can be used. Larger sized tubes can also be used, but at some point the size interferes with nebulization.

Surrounding a portion 44 of the sheath liquid tube 20 is a gas feed tube 46 connected at its proximal end 48 to a gas supply 50 which supplies a gas flow 52. The gas tube 46 terminates at a tapered end 54 having an orifice 56. The nebulizer nozzle outlet 42 is located at or near the orifice 56 and is preferably centered with respect to the orifice 56 and located a distance "d" with respect to the orifice 56 so that the gas flow 52 and the combined fluid flow can produce an aerosol 58. The distance "d" is variable or adjustable and can place the nozzle outlet 42 either before or after the orifice 56 allowing optimization of the quality of the aerosol, i.e. optimization of the size of the droplets in the aerosol. Depending on the size of the orifice 56, the distance "d", the length and $id_2$ of nebulizer nozzle 38, the viscosity and surface tension of the combined fluid flow entering the nebulizer nozzle 38, the gas pressure difference across the orifice 56 and the flow rate of the gas flow 52, the nebulizer 11 will have a natural self-aspiration rate. The difference between the first flow resistance and the second flow resistance, the gap 32, the sheath liquid supply 22 and overflow 24 allow the interface 10 to use a varying amount of sheath fluid flow 29 such that the sum of sheath fluid flow 29 and the sample feed flow 12 remains constant and substantially matches the natural self-aspiration rate of the nebulizer 11, without altering the original feed rate of the sample feed flow 12.

Generally, the second flow resistance should be substantially negligible with respect to the first flow resistance, i.e.,. the ratio of the first flow resistance to the second flow resistence is between about 100 and about 1,000,000. Preferably, the first flow resistance is much larger than the second flow resistance and their ratio is between about 100 and about 100,000, particularly, between about 500 and about 100,000 and especially between about 1,000 and 100,000. Generally, the distance "d" will depend on the size of the nebulizer nozzle, but for interfaces involving capillary separation techniques, the distance "d" is less than 10 mm, preferably less than 5 mm and especially less than 1 mm.

The term "substantially matches" means that the combined fluid flow rate entering the nozzle is generally within about ±50% of the self-aspiration rate of the interface, preferably within about ±25%, particularly within about ±10%, especially within about ±5% of the self-aspiration rate of the interface. Of course for optimum performance, the combined fluid flow rate should exactly equal or match the self-aspiration rate of the interface. The interfaces of the present invention allow this matching to occur automatically because the sheath fluid is supplied so that the interface utilizes only the amount of sheath fluid that is needed, when combined with the sample fluid flow in the gap,to exactly match the natural self-aspiration rate of the interfaces.

Figure 1A:
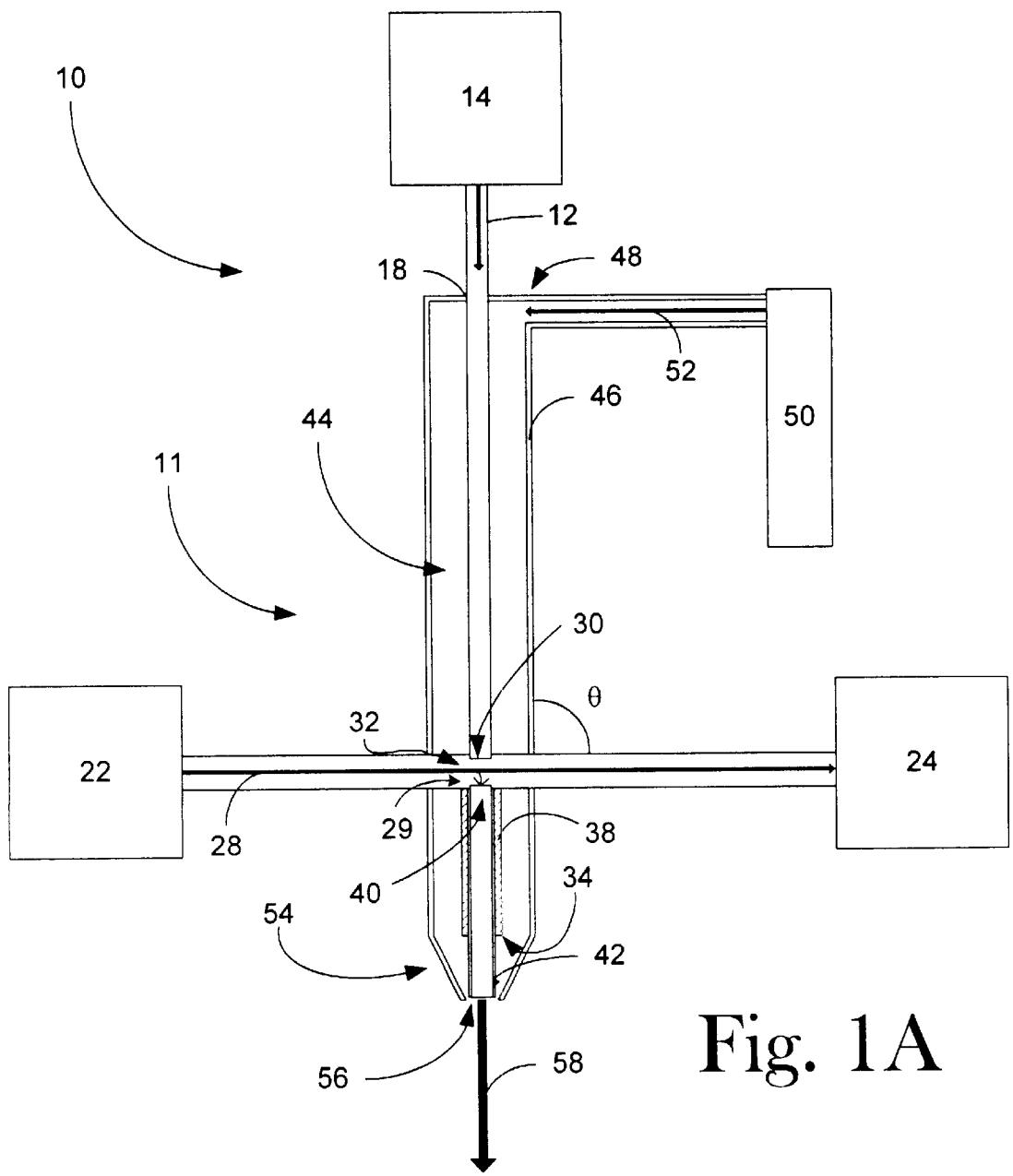

Referring now to FIG. 1A, an alternate construction of the interface 10 of FIG. 1 is shown to includes a sheath liquid feed tube 20 oriented at an angle θ with respect to the inlet tube 18. The sheath liquid feed tube 20 is connected at its proximal end 26 to a sheath liquid supply 22 and a sheath liquid overflow 24. The sheath liquid feed tube 20 is positioned at or near the gap 32 so that the sheath liquid flow 29 can supply the self-aspiration flow 29 to the nozzle 38 with the remainder going to the overflow 24. The angle θ is shown here as a 90°, but can be any angle greater than 0° (the alignment shown in FIG. 1) to less than 180° and will depend on manufacturing and design choices. Of course, any of the other preferred embodiments shown below can include an angled sheath liquid feed system.

Figure 2:
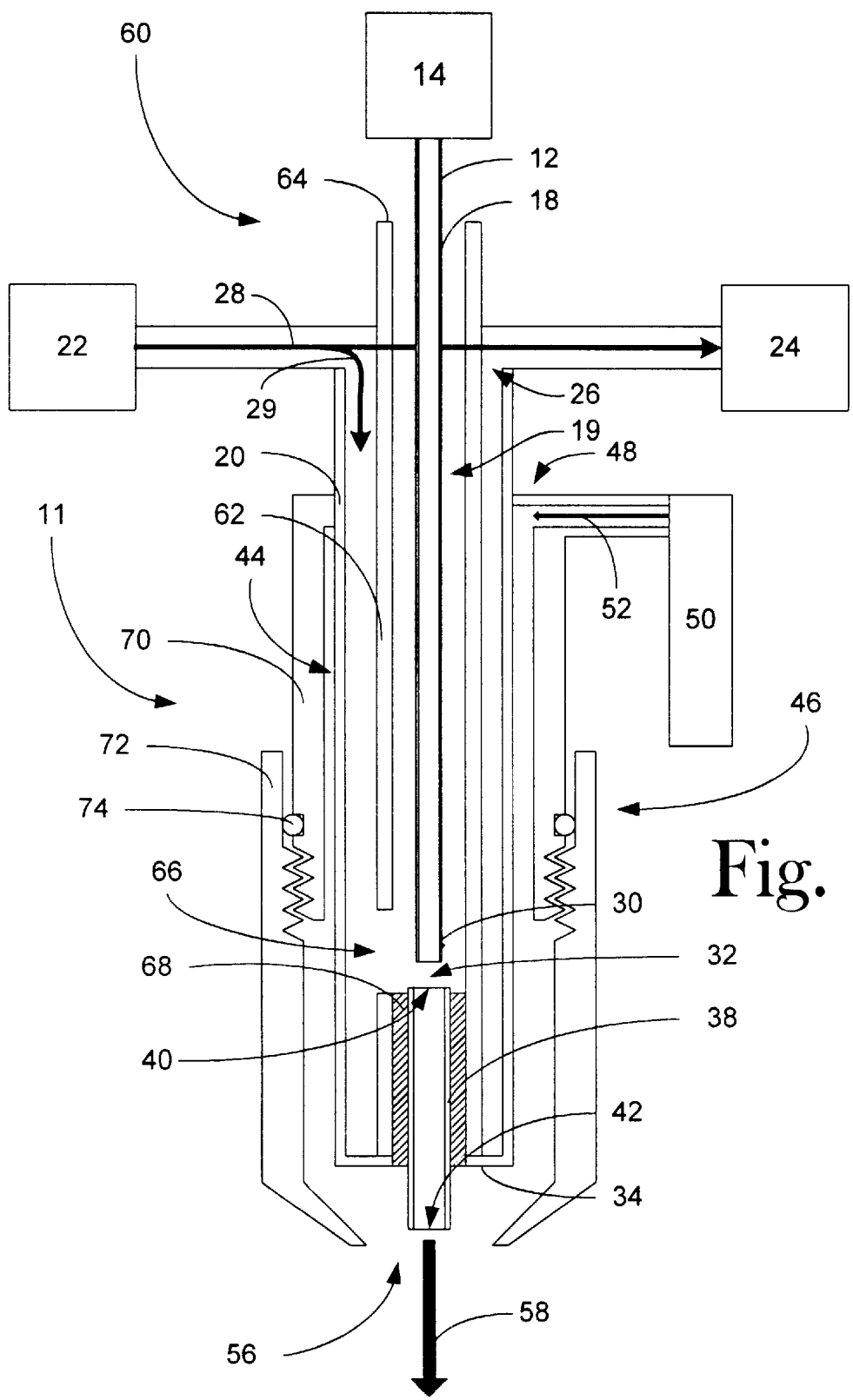
FIG. 2 is a cross-sectional and block diagram of another embodiment of an interface of the present invention.

Referring now to FIG. 2, another preferred embodiment of an interface of the present invention generally 60 is shown to include a nebulizer 11, a sample feed or separation apparatus effluent 12 exiting a separation or analyte delivery apparatus 14. The sample feed enters the interface 60 via a sample feed inlet tube 18 having an internal diameter $id_1$ and a first flow resistance.

A sheath liquid feed tube 20 surrounds a portion 19 of the feed tube 18. The sheath liquid feed tube 20 is connected to a sheath liquid supply 22 and a sheath liquid overflow 24 at its proximal end 26. The tube 18 terminates at its distal end 30 in a gap 32. In the gap 32, the sample feed or effluent 12 and the sheath liquid feed 29 are combined. The sheath tube 20 is closed at its distal end 34 at any position downstream of the gap 32. The gap 32 ends at a nebulizer nozzle 38 having an inlet 40, an outlet 42 and an internal diameter $id_2$. As stated previously, the nebulizer nozzle 38 should be as short a commercially practical. The combined fluid flow (the sum of the sample flow 12 and sheath flow 29) enters the nebulizer nozzle 38 at its inlet 40 and exits at its outlet 42. As with the interface of FIG. 1, $id_1$ and $id_2$ can be the same or different, but preferably, $id_2$ is equal to or greater than $id_1$ and particularly, $id_2$ is greater than $id_1$ and have the values set forth above.

Surrounding the feed tube 18 and the nebulizer nozzle 38 is a support tube 62 having a proximal end 64 that can be sealed around the feed tube 18. The support tube 62 has at least one opening 66 therein positioned at or near the gap 32. The at least one opening 66 ensures an even sheath liquid flow into the gap 32 and by having a second flow resistance which is smaller than the first flow resistance, together with the sheath liquid supply 22 and overflow 24, it prevents the nebulization-induced suction from adversely affecting the widths of the analyte bands in the analyte-containing feed flow 12. The nozzle tube 38 is positioned within the support tube 62 by an inert member 68 which can be a seal, an inert cement or adhesive.

Surrounding a portion 44 of the sheath liquid tube 20 and support tube 62 is a gas feed tube 46 connected at its proximal end 48 to a gas supply 50 which supplies a gas flow 52. The gas tube 46 includes a threaded top section 70 and a threaded bottom section 72 which are sealed with respect to each other with O-ring 74. The gas tube 46 terminates in an orifice 56. The nozzle tube outlet 42 is located at or near the orifice 56. Preferably, the outlet 42 is centered with respect to the orifice 56 and located a distance "d" with respect to the orifice 56 so that the gas flow 52 can combine with the combined fluid phase flow to produce an aerosol 58. The threaded top section 70 and the threaded bottom section 72 allow for control and adjustment of the distance "d" between the exit 42 and the orifice 56.

Figure 3A:
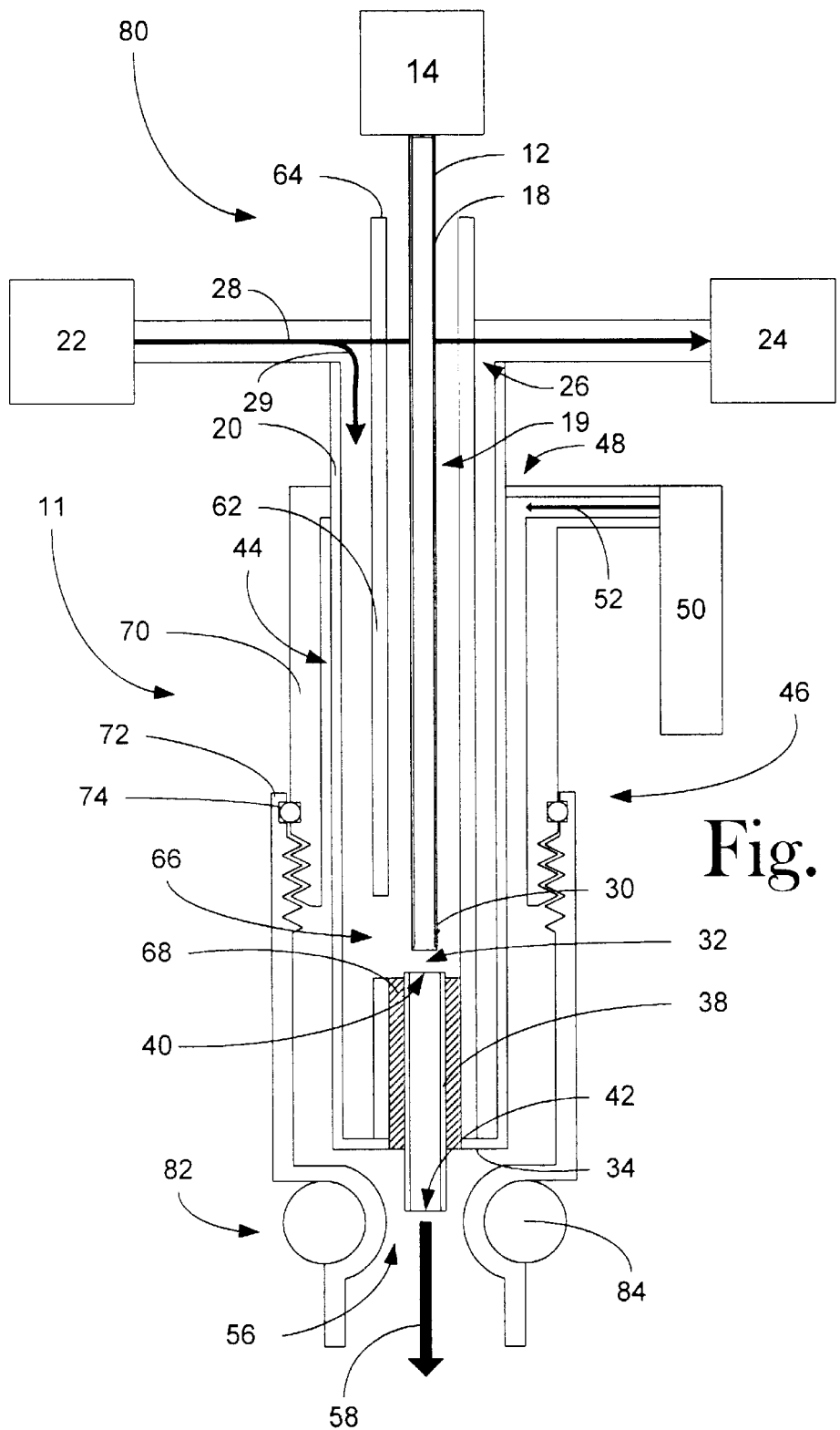
FIGS. 3A and 3B are cross-sectional and a lock diagram of yet another embodiment of an interface of the present invention.

Referring now to FIG. 3A, another preferred embodiment of an interface of the present invention generally 80 is shown to include a nebulizer 11, a sample feed or separation apparatus effluent 12 exiting a separation or analyte delivery apparatus 14. The sample feed enters the interface 80 via a sample feed inlet tube 18 having an internal diameter $id_1$ and a first flow resistance.

A sheath liquid feed tube 20 surrounds a portion 19 of the feed tube 18. The sheath liquid feed tube 20 is connected to a sheath liquid supply 22 and a sheath liquid overflow 24 at its proximal end 26. The tube 18 terminates at its distal end 30 in a gap 32. In the gap 32, the sample feed or effluent 12 and the sheath liquid feed 29 are combined. The sheath tube 20 is closed at its distal end 34 at any position downstream of the gap 32. The gap 32 ends at a nebulizer nozzle 38 having an inlet 40, an outlet 42 and an internal diameter $id_2$. Again, the same preferred relationship between $id_1$ and $id_2$ as set forth for the interfaces described in FIGS. 1 and 2 apply here as well.

Surrounding the feed tube 18 and the nebulizer nozzle 38 is a support tube 62. The support tube 62 has at least one opening 66 therein positioned at or near the gap 32. The sheath liquid tube 20 and opening 66 together have a second flow resistance which, in combination with the sheath liquid supply 22 and overflow 24 allow the nebulizer 11 to be self-adjusting and free-flowing as described previously. The nebulizer nozzle 38 is positioned within the support tube 62 by an inert member 68 which can be a seal, an inert cement or adhesive.

Surrounding a portion 44 of the sheath liquid tube 20 is a gas feed tube 46 connected at its proximal end 48 to a gas supply 50 which supplies a gas flow 52. The gas tube 46 as in FIG. 2, has a threaded top section 70, a threaded bottom section 72, sealed by an O-ring 74 and terminates at a constriction 82 which forms an orifice 56. The constriction 82 is formed in the bottom section 72 of the gas tube 46 by an element 84 which deforms the tube 46 inward decreasing its internal diameter and thereby restricting the gas flow into the orifice 56 to form an aerosol 58 of the combined fluid flow. Again, the nozzle tube outlet 42 is located at or near the orifice 56 and preferably, the outlet 42 is centered with respect to the orifice 56 and is located at a distance "d" with respect to the orifice 56 so that the gas flow 52 can combine with the combined fluid flow to produce an aerosol 58 as it exits the nebulizing nozzle 38. Again, the threaded sections 70 and 72 of the gas inlet tube 46 allow for adjustment and control of the distance "d".

When the interfaces described in FIGS. 1–3A are used to interface with separation techniques that utilize an electric field, grounding generally is provided on the sheath liquid supply system, e.g., the sheath tube 20, the sheath supply 22 or the overflow 24; provided that they are made of a conductive material.

When grounding is provided in the sheath liquid supply system, ions leaving the distal end 30 of the tube 18 can move radially causing additional band broadening prior to nebulization. This additional band broadening can be reduced or eliminated by grounding at the nozzle 38 which is made of a conductive material, while tubes 18, 20, 46 or upper part 70 and 62 and member 68 are made of non-conductive materials. Conductive materials include metals or alloys, conductive polymers or conductive ceramics, or mixtures or combinations thereof; while non-conductive materials include non-conductive polymers or ceramics, or mixtures or combinations thereof.

Figure 3B:
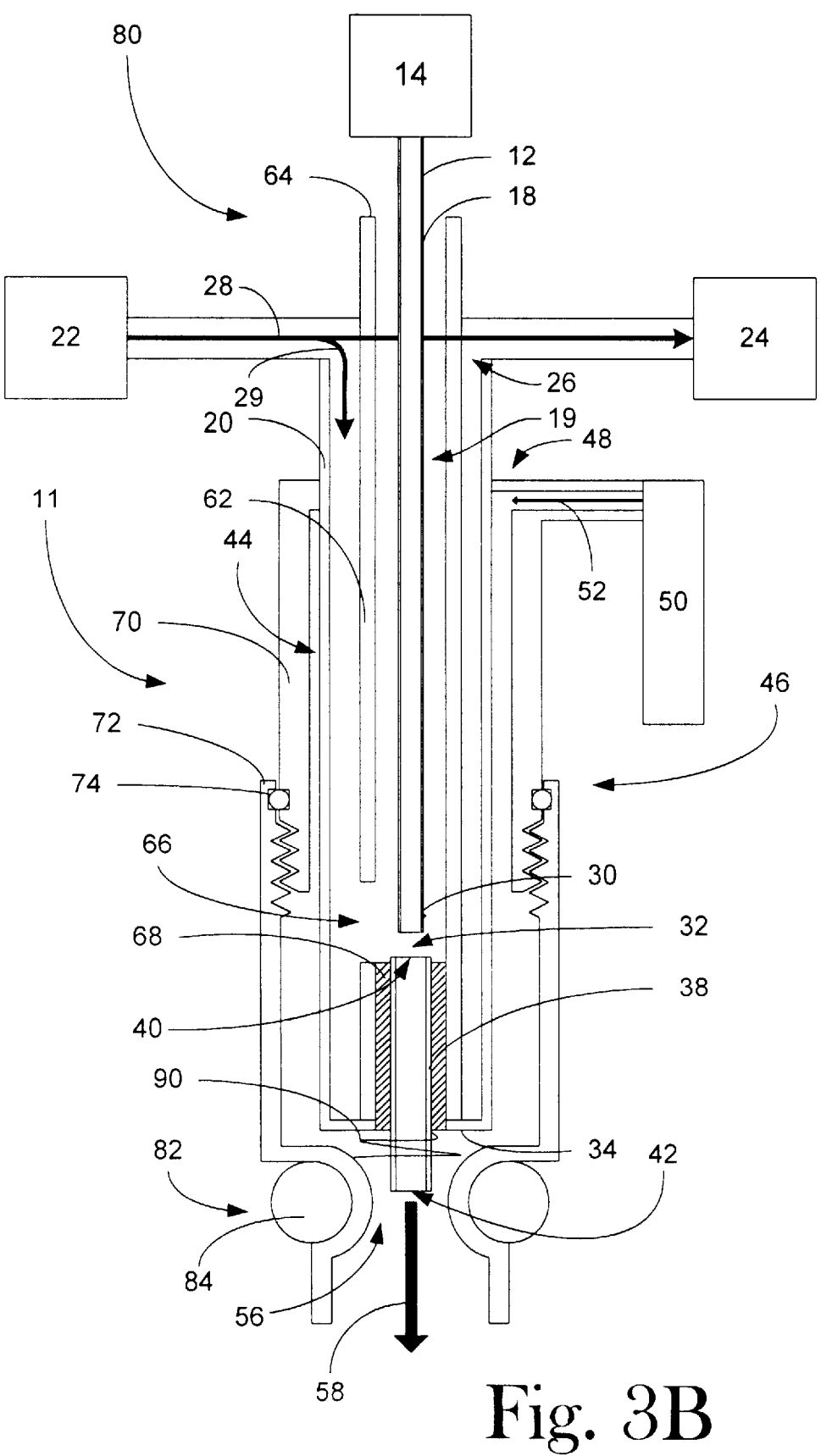

For example, referring now to FIG. 3B, a preferred grounding arrangement is shown which grounds to the nozzle 38. A wire 90 is electrically connected to the nozzle 38 and to bottom section 72 of tube 46, while permitting the adjustment of the distance "d". Preferably, the wire 90 is a spring. The nozzle 38, the section 72 and the wire 90 are constructed of electrically conductive materials.

Preferred Embodiments of Instrument Systems Incorporating the Interface

Figure 4:
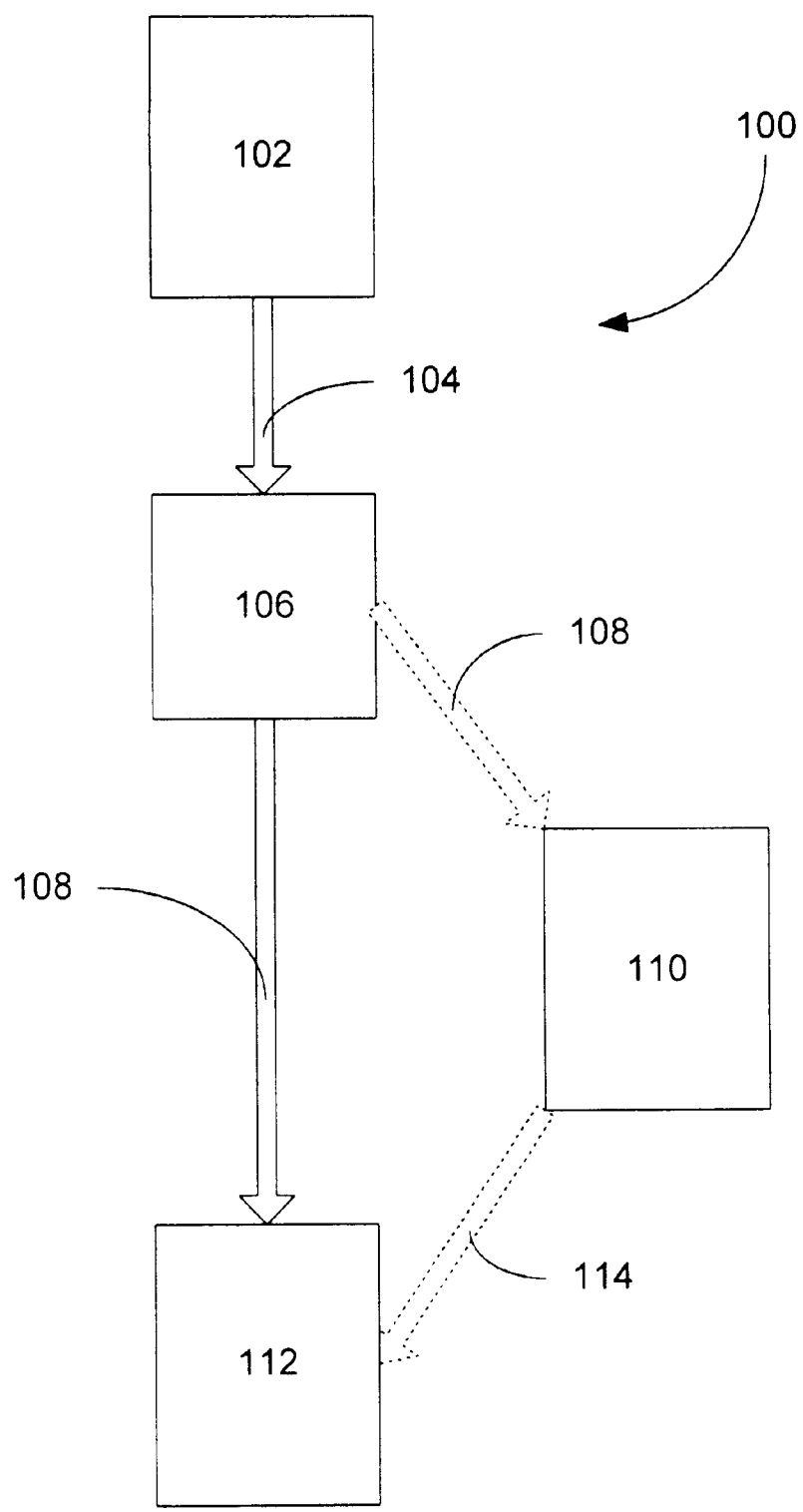
FIG. 4 is a block diagram of an analytical instrument incorporating the interface of the present invention.
Figure 5:
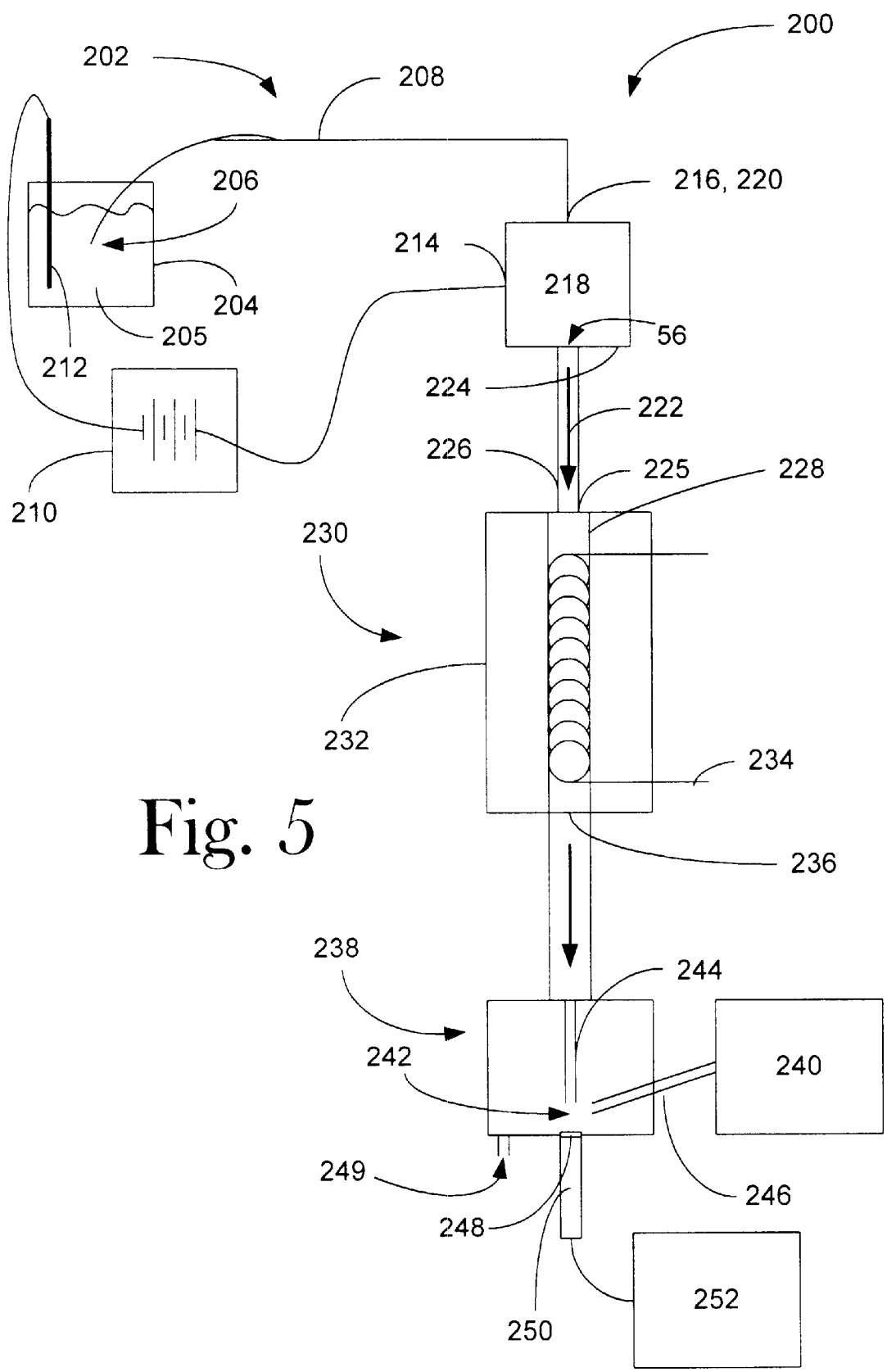
FIG. 5 is a block diagram of a nitrogen chemiluminescence instrument incorporating the interface of the present invention.

Referring now to FIG. 4, an analytical system generally 100 is shown to include a fluid phase separation or analyte delivery apparatus 102. A fluid phase effluent 104 from the apparatus 102 is forwarded to an interface 106 of the present invention. The interface 106 generally combines the fluid phase effluent 104 with a sheath fluid and then converts the resulting combined fluid flow into an aerosol 108 using a gas. The aerosol 108 can be directly deposited on a surface (not shown), forwarded to a sample component conversion apparatus 110 or forwarded to a detection apparatus 112. If the aerosol 108 is forwarded to the conversion apparatus 110, then the sample components in the aerosol 108 are transformed into a conversion unit effluent 114 and forwarded to the detection apparatus 112. The conversion unit effluent 114 will include compounds which can be detected, post conversion, in the detection apparatus 112.

Preferred separation apparatus include, without limitation, analytical or preparative chromatographic apparatus, analytical or preparative electrophoretic apparatus, analytical or preparative field flow fractionation apparatus, etc. Preferred analyte delivery apparatus include, without limitation, sample loops, sample valves, sample dispensers, flow injection analyzers, etc. Preferred detection apparatus include, without limitation, detectors generally known in the art such as gas chromatographic detector systems (e.g., ionization detectors, electron capture detectors, photometric detectors, etc.), mass spectrometric detector systems, evaporative light scattering detector systems, condensation nucleation light scattering detector systems, nitrogen-selective chemiluminescene detector systems and sulfur-selective chemiluminescene detector systems. Preferred overall analytical systems include, without limitation, capillary electrophoresis-inductively coupled plasma-mass spectrometers (CE-ICP-MS), capillary electrophoresis-microwave coupled plasma-mass spectrometers (CE-MCP-MS), capillary electrophoresis-evaporative light scattering detectors (CE-ELSD), capillary electrophoresis-condensation nucleation light scattering detectors (CE-CNLSD), capillary electrophoresis-chemiluminescence nitrogen detectors (CE-CLND), capillary electrophoresis-chemiluminescence sulfur detectors (CE-SCLD) or the like.

Referring now to FIG. 5, a preferred analytical system of the present invention generally 200 is shown to include a capillary electrophoresis (CE) separation apparatus 202. The CE apparatus 202 includes a solution vessel 204 containing an electrolyte 205 into which a first end 206 of a capillary tube 208 is placed. A high voltage generated by a voltage source 210 is placed across the capillary tube 208. One of its electrodes 212 is coupled to the vessel 204 and its other electrode 214 is coupled to an interface 218 of the present invention.

A sample is then introduced into the first end 206 of the capillary 208. The components of the sample are then separated in the capillary tube under the influence of the electric field applied across the capillary tube. As the sample components exit the capillary 208 at its distal end 216, the components enter an interface 218 at its inlet 220. The interface 218 can be any of the interfaces described above.

As described above, the sample components are generally combined with a sheath fluid in the interface 218 under conditions where the flow of the sample component from the capillary tube 208 is not substantially adversely affected by the supplied sheath fluid flow or the nebulization-induced suction of the interface. As the sample component combined with the sheath fluid exits the interface 218 through the orifice 56, it is nebulized with an oxidizing gas to produce an oxygen-rich aerosol 222. The preferred oxidizing gas is oxygen gas or an oxygen-containing gas mixture such as an oxygen-argon gas mixture.

The orifice 56 is connected to a first end 224 of a connecting tube 226 which, at its second end 225, is operatively connected to or integral with a combustion tube 228 of a combustion apparatus 230. The connecting tube 226 can include an auxiliary gas inlet connected in a gas tight fashion to a gas source by a gas supply line having a flow, and/or pressure controller associated therewith (not shown). The auxiliary gas may be used to prevent the oxygen-rich aerosol from contacting the inner walls of the connecting tube and to help forward the oxygen-rich aerosol to the combustion chamber. The auxiliary gas is preferably an inert gas.

The combustion apparatus 230 also includes an outer housing 232 containing a temperature controllable heater 234 which surrounds the combustion tube 228. The heater 234 is designed to maintain a combustion zone at a given elevated temperature. The heater 234 can have a single or multiple heater elements so that different portions of the combustion tube 228 can be separately maintained at different temperatures. Of course, the combustion zone can be the entire interior of the combustion tube 228 or any portion thereof. The connecting tube 226 and the combustion tube 228 are preferably formed from quartz, ceramic or the like. Preferably, the orifice 56 of the interface 218 should be positioned as close as possible to the combustion tube without causing clogging or deterioration of the orifice 56.

The heater 234 maintains the combustion zone at an elevated temperature sufficient to promote partial, near complete, or complete oxidation of oxidizable sample components and/or solvent(s) contained in the oxygen-rich aerosol 222. Preferably, the heater 234 is an electric heating element. Of course, any heating apparatus can be used; provided, however, that the apparatus is capable of adequately maintaining the oxidation zone at a given elevated temperature.

The combustion gases formed in the apparatus 230 exit through a chamber outlet 236 and are forwarded to a nitrogen-selective chemiluminescence detector (CLND) 238. The CLND 238 includes an ozone generator 240 which supplies ozone to a light-tight chemiluminescence reaction chamber 242. The reaction chamber 242 has a sample inlet tube 244 and an ozone inlet tube 246 positioned in front of a window 248 and a gas exit 249. The exit 249 can be connected to a vacuum unit (not shown). Light generated by the ozone reaction with NO passes through the window 248 which generally includes an optical filter (not shown), into a light-sensing apparatus, such as photomultiplier tube 250. The photomultiplier tube 250 is in electrical communication with a data acquisition device 252 which converts a signal output of the photomultiplier tube 250 into an output evidencing the detection of nitrogen containing sample components. The signal output is proportional to the amount of each nitrogen containing sample component in the sample. Other processes and detectors can also be used including, without limitation, those described in U.S. Pat. Nos. 4,018,563, now Re. 34,668; 4,352,779; 4,678,756; 4,914,037; 4,950,456; 5,227,135; 5,310,683; 5,330,714; and 5,424,217, incorporated herein by reference.

If sulfur-selective chemiluminescence detection (CLSD) is to be performed separately or in addition to nitrogen-selective chemiluminescence detection, then the oxidized sample is passed through a reductive furnace where the oxidized sample is partially reduced generally by hydrogen gas. The reduction is controlled so that sulfur oxides are reduced to ozone-reactive sulfur species, while the NO concentration is not reduced below its detection limit. Further details on detecting sulfur-selective chemiluminescence or detecting simultaneously nitrogen-selective and sulfur-selective chemiluminescence is described in co-pending application No. 08/760, 247 entitled "Apparatus and Methods for Near Simultaneous Chemiluminescent Sulfur and Nitrogen Detection" filed Dec. 4, 1996, now U.S. Pat. No. 5,916,523, incorporated herein by reference.

The apparatus and method of this invention are particularly well-suited to serve as a substantially self-adjusting, free-flowing pneumatic nebulizer sample interface between a fluid phase separation or analyte delivery apparatus and a gas phase conversion/detection apparatus. The interface is especially well-suited for interfacing capillary electrophoresis separation apparatus to gas phase detection apparatus such as MS, ICP-MS, MCP-MS, CLND, CLSD, etc.

EXAMPLES

The following examples are included for the sake of completeness of disclosure and to illustrate the scope or teaching of this disclosure.

Example 1

This example illustrates the use of the pneumatic nebulizer interface 80 shown in FIGS. 3A for the coupling of a capillary electrophoretic separation system to a Model CLND 7060 nitrogen-selective chemiluminescence detector system (ANTEK Instruments, Inc., Houston, Tex.).

A 75 $\mu$m internal diameter, $L_{total}$=59.6 cm long fused silica capillary (Polymicro Technologies, Phoenix, Ariz.) was connected to a 2 mL inlet vial. A 0.5 mm long section of the protecting polyimine coating was removed from the capillary to create a window for the UV detector a distance $L_{UV}$=29.5 cm away from its inlet. The window portion of the capillary was inserted into the capillary electrophoretic cell holder of a Model 200 (Linear, Reno, Nev.) UV detector, which was operated at 214 nm. The outlet end of the fused silica capillary was inserted into the pneumatic interface 80 in FIG. 3A and acted as the inlet line 18. The capillary and the inlet vial were filled with a 50 mM citric acid solution titrated to pH 2.6 with LiOH. A 35 mm long, 0.5 mm diameter platinum wire electrode was inserted into the inlet vial and connected to the high voltage terminal of a Model EH30 power supply (Glassman, Whitehouse Station, N.J.). The sheath liquid delivery tube 26 of the interface 80 in FIG. 3A was connected to the ground terminal of the power supply to close the electrical circuit for the electrophoretic separation. The sheath liquid was 10 mM acetic acid; it was pumped at a flow rate of 300 $\mu$L/min by a Model 2100 liquid chromatography pump (Varian, Walnut Creek, Calif.), acting as the sheath liquid delivery unit 22 in FIG. 3A, through a $\frac{1}{16}$" cross liquid chromatographic fitting (Valco, Houston, Tex.) whose respective arms acted as elements 24, 26 and 64 in FIG. 3A. The nebulizing gas (52 in FIG. 3A) was pure oxygen, delivered into the element 46 at 60 psi pressure, resulting in a nebulizing gas flow rate of 180 mL/min through the orifice 56. The vertical positions of the inlet and outlet ends of the fused silica capillary were carefully adjusted to the same level to ensure that syphoning-induced flow did not occur in the fused silica capillary. Analytes were injected by 0.5 psi nitrogen gas pressure at the inlet of the capillary.

The temperature in the oven of the CLND 7060 was maintained at 1050 C. The interface 80 was connected to the inlet end of the oven. The electric signals from the UV detector and the CLND 7060 detector were monitored by an AD406 dual channel data collection system (Beckman-Coulter, Fullerton, Calif.), operated under control of the Gold Ver. 8.1 data acquisition software package (Beckman-Coulter, Fullerton, Calif.), which was running on a 486DX2 personal computer (Computer Access, College Station, Tex.).

Figure 6:
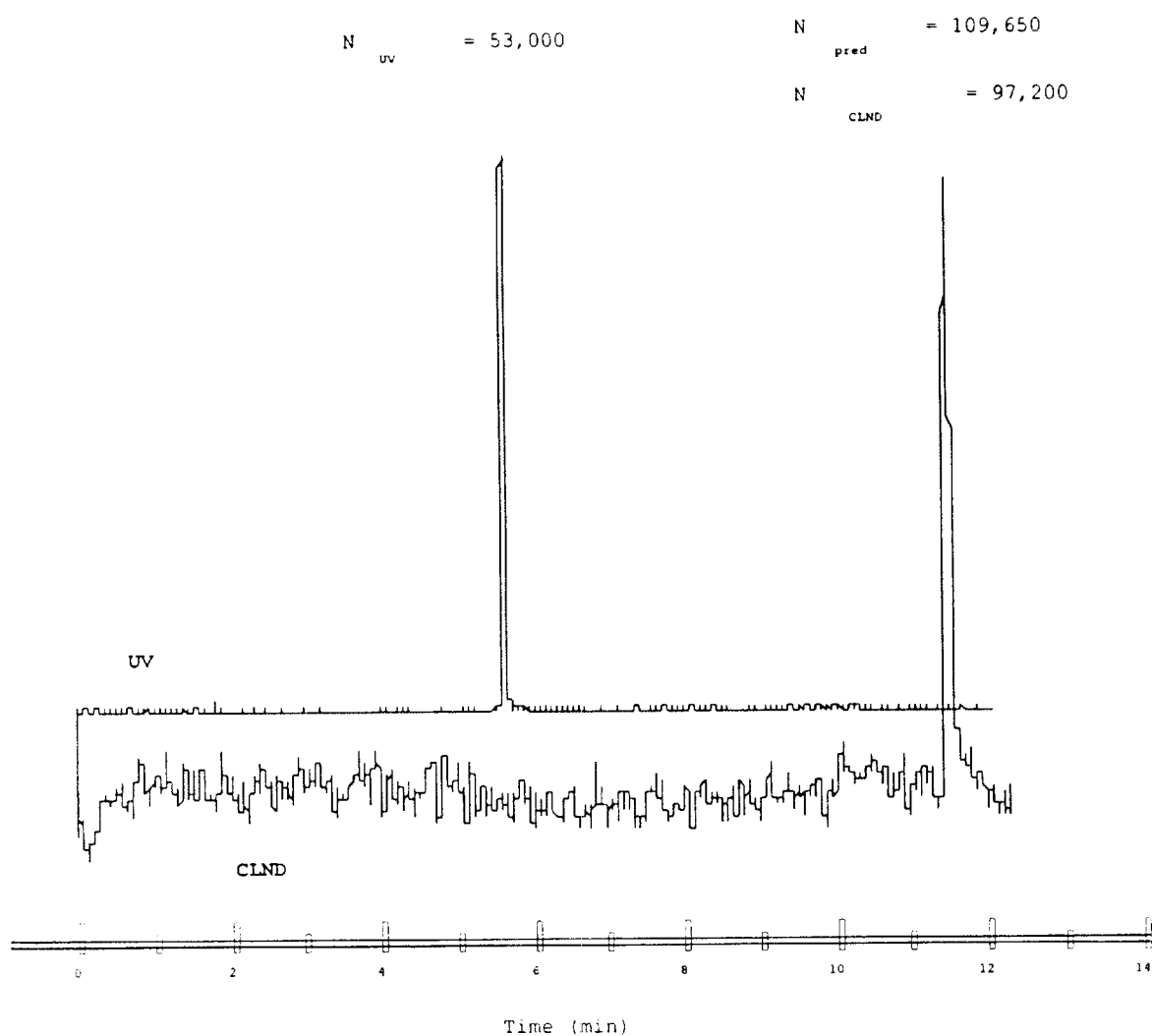
FIG. 6 is a detector trace obtained for an N,N-dimethylformamide (DMF) sample injected into a capillary electrophoretic system and introduced through the interface of the present invention into a nitrogen chemiluminescence detector.

A 789 $\mu$m long band of a 30 mM N,N-dimethylformamide sample was injected into the inlet end of the fused silica capillary and a separation potential of 10 kV was applied for 12 min. The electropherograms recorded by the UV and CLND detectors are shown in FIG. 6. The number of theoretical plates characterizing the separation efficiency of the system were calculated as known in the art (see, e.g., B. L. Karger, L. R. Snyder, Cs. Horvath, An Introduction to Separation Science, Wiley, N.Y., 1973, pages 135–138) from the UV and CLND detector traces as $N=5.545(t/w_{0.5})^2$, where t is the time at the peak apex and $w_{0.5}$ is the width of the peak at half height in time units. Also, $N=L^2/(\sigma^2_{tot})$, where L is the length of the capillary in cm units and $\sigma^2_{tot}$ is the recorded total peak variance in cm² units. Furthermore, due to the additivity of variances, it holds that $\sigma^2_{tot}=\sigma^2_{inj}+\sigma^2_{diff}+\sigma^2_{det}$, where $\sigma^2_{inj}$ is the peak variance due to the finite length of the injected sample band, $\sigma^2_{diff}$ is the peak variance due to longitudinal diffusion and $\sigma^2_{det}$ is the peak variance due to the finite length of the detector cell. Since the finite length of the injected sample band and the finite length of the detector cell are $l_{inj}$ and $l_{det}$, respectively, $\sigma^2_{inj}$ and $\sigma^2_{det}$ can be calculated as $\sigma^2_{inj}=l^2_{inj}/12$, and $\sigma^2_{det}=l^2_{det}/12$. The diffusional peak variance, $\sigma^2_{diff}$ can be obtained as $\sigma^2_{diff}=2Dt$, where D is the diffusion coefficient of the analyte and t is the peak apex time.

The number of theoretical plates calculated from the UV detector trace in FIG. 6 is $N_{UV}$=53,000, from which $\sigma^2_{tot,UV}$ becomes $\sigma^2_{tot,UV}$=1.642×10⁻² cm². Since $l_{inj}$=0.0789 cm and $l_{det}$=0.05 cm, one can calculate $\sigma^2_{inj}$=5.188×10⁻⁴ cm², and $\sigma^2_{det}$=2.083×10⁻⁴ cm². This yields $\sigma^2_{diff,UV}$=1.5693×10⁻² cm². Since the peak apex time is 343 s, this results in an observed effective diffusion coefficient of D=2.29×10⁻⁵ cm²/s. Since the peak is detected at the end of the capillary with the CLND 7060 detector at 690 s, and since the time delay caused by the CLND is less than 1 s, the calculated $\sigma^2_{diff,end}$ becomes $\sigma^2_{diff,end}$=3.1568×10⁻² cm², and $\sigma^2_{tot,end}$ becomes $\sigma^2_{tot,end}=\sigma^2_{inj}+\sigma^2_{diff,end}+\sigma^2_{det}$=3.2295×10⁻² cm². From this, the predicted number of theoretical plates at the end of the column is $N_{tot,end}$=109,650. The number of theoretical plates calculated directly from the CLND trace is 97,200, which represents a loss of only 11.4% in separation efficiency. This loss is caused by the combined effects of the pneumatic nebulizer interface 80 and the CLND 7060 nitrogen detector.

Example 2

Figure 7:
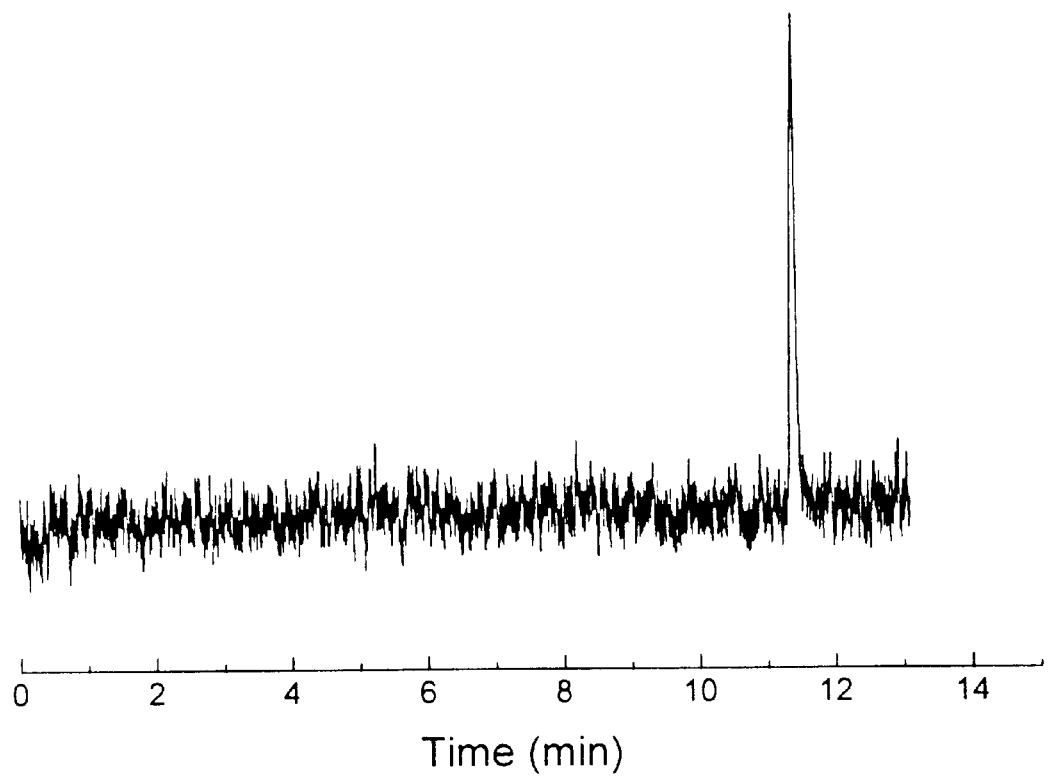
FIG. 7 is a detector trace obtained for an adenosine, cytosine, guanine and uracil-containing sample injected into a capillary electrophoretic system and introduced through the interface of the present invention into a nitrogen chemiluminescence detector.

This example demonstrates that under optimum conditions, this interface preserves the high efficiency of the electrophoretic separation unit coupled to it, and that theoretical plate counts in excess of 10⁵ can be achieved. The method used to calculate the theoretical plate count is the same as described in Example 1. The experimental setup is the same as the setup described in Example 1. The optimization of the interface means finding the capillary position that is as near to the nebulizing nozzle 38 as possible without causing any laminar flow in the separation capillary, because laminar flow cause band broadening or dispersion. The recorded CLND 7060 detector trace are shown in FIG. 7. The theoretical plate count was calculated to be 113,598.

Example 3

This example illustrates the use of the integrated analytical system consisting of a capillary electrophoretic subsystem, the nebulizer interface 80 in FIG. 3A, and the CLND 7060 detector subsystem for the electrophoretic separation and nitrogen-selective detection of four nucleoside bases, adenine (A), cytosine (C), guanine (G) and uracil (U).

Figure 8:
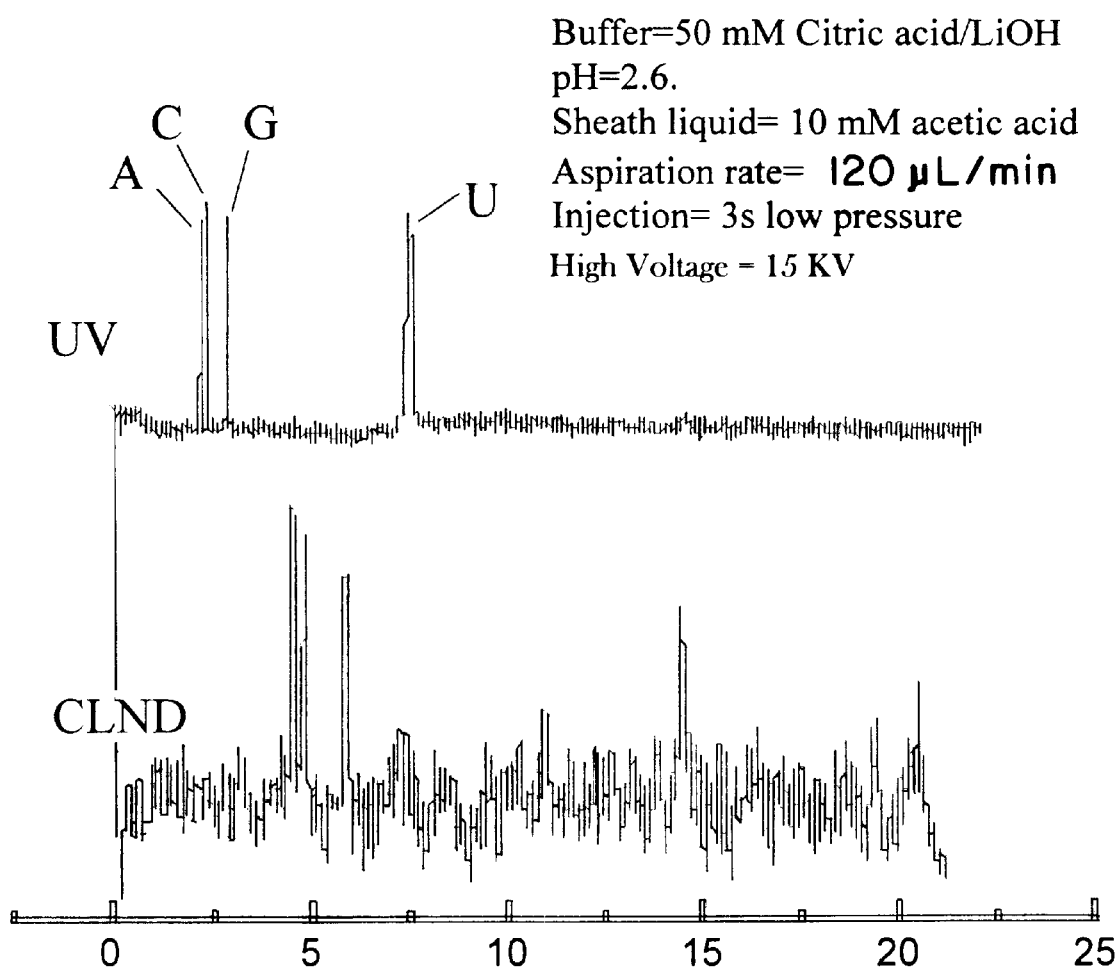
FIG. 8 are UV and CLND detector traces obtained for an adenosine, cytosine, guanine and uracil-containing sample injected into a capillary electrophoretic system and introduced through the interface of the present invention into a nitrogen chemiluminescence detector.

The same experimental set-up was used as in Example 1, except that $L_{total}$=48.8 cm, $L_{UV}$=23.9 cm. The separation potential was 15 kV. The self-aspiration rate of the interface 80 was 120 μL/min. The injected sample contained 2.07 pmol adenine, 2.08 pmol cytosine, 2.78 pmol guanine and 3.79 pmol uracil. The recorded UV detector and CLND 7060 detector traces are shown in FIG. 8. The signal-to-noise ratio in the UV detector trace was calculated to be about 10, while it was found to be about 3 in the CLND trace. The detector traces indicate that peak resolution that can be observed in the UV detector was preserved as the analytes pass through the interface 80 and the CLND 7060 detector.

Example 4

This example illustrates the use of the integrated analytical system consisting of a capillary electrophoretic subsystem, the nebulizer interface 80 in FIG. 3A, and the CLND 7060 detector subsystem for the electrophoretic enrichment and simultaneous nitrogen-selective detection of four antibiotics, kanamycin, streptomycin, tobramycin and neomycin.

The same experimental set-up was used as in Example 1, except that $L_{total}$=50 cm, $L_{UV}$=25 cm, and the internal diameter of the capillary was 100 μm. The self-aspiration rate of the interface 80 was 100 μL/min, the nebulizing gas flow rate was 100 mL/min. The capillary was first rinsed with 5 column volumes of 1 M HCl solution, followed by 5 column volumes of deionized water, followed by five column volumes of 1 M NaOH solution and finally, by five column volumes of 0.01% w/w Polybrene dissolved in 50 mM, pH 4.5 formate buffer solution. The Polybrene solution was then rinsed off the capillary by five column volumes of 50 mM, pH 4.5 formate buffer solution. The capillary was then conditioned by electrophoretically moving the formate buffer solution through it by −5 kV for 20 min. The capillary was then filled, sequentially, with a pH 4 HCl solution of each antibiotic at varying concentrations. The −20 kV electrophoretic potential was then applied until the HCl solution became replaced by the formate buffer in the capillary. Then the separation potential was disconnected and the content of the capillary was moved into the nebulizer by the formate buffer solution at a linear velocity of 0.35 cm/s. The CLND signal was recorded and plotted as a function of the original concentration of the antibiotic solution, yielding the calibration curves shown in FIG. 9.

Figure 9:
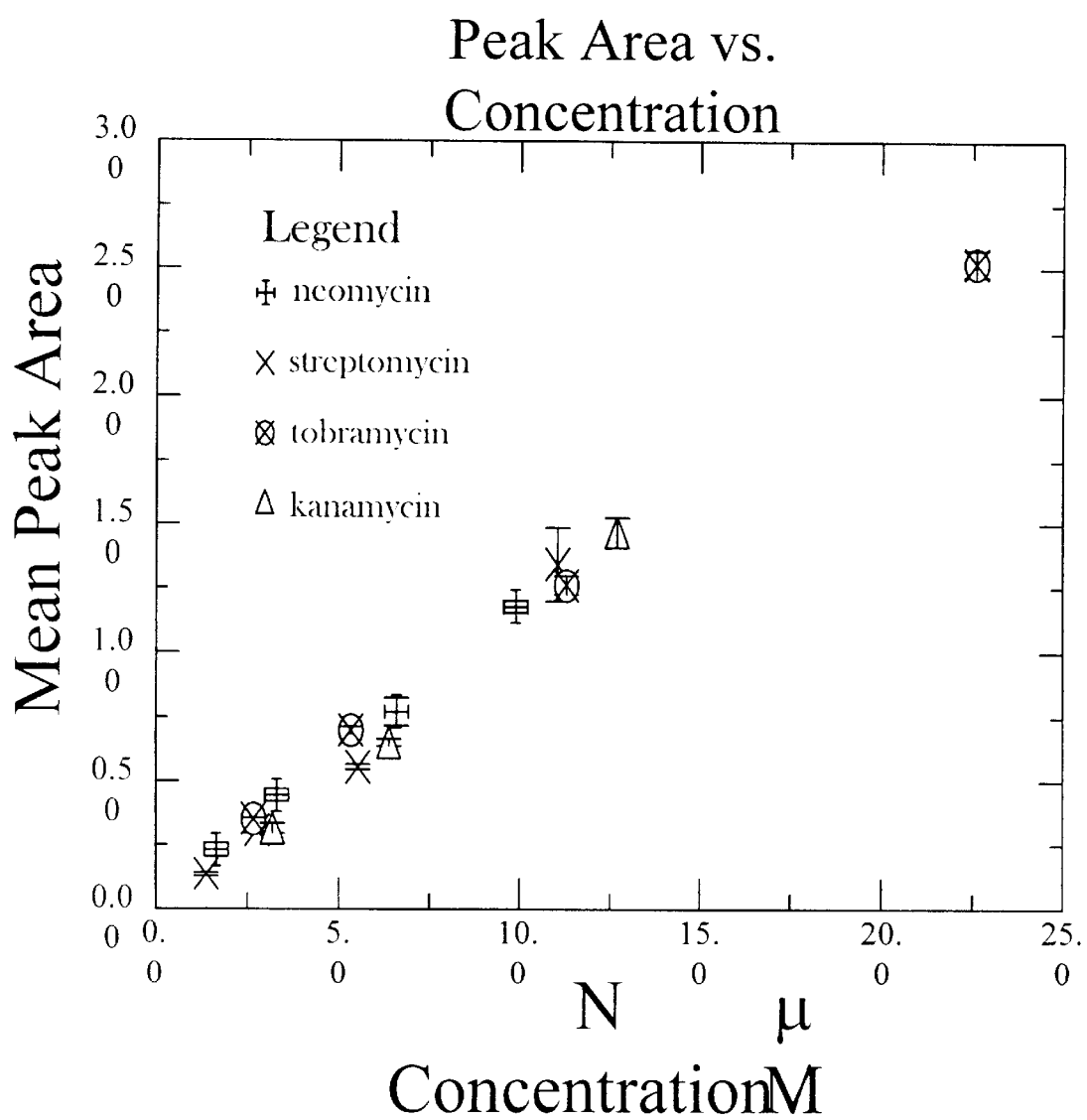
FIG. 9 depicts a plot of the CLND signal as a function of the original concentration of an antibiotic solution, yielding the calibration curves shown in FIG. 9.

FIG. 9 indicates that each antibiotic could be detected at the 2 μM N concentration level and that the molar nitrogen response factors were identical for each of the antibiotics studied.

Example 5

This example illustrates a technique to determine the presence of pressure driven flow in the separation capillary. The technique utilizes the principles of pressure mediated capillary electrophoresis (PreMCE). The technique is set forth as the steps that are performed prior to any actual use of a capillary electrophoresis apparatus connected to a detector via the nebulizer. The example also illustrates the UV and chemiluminescent nitrogen detector (CLND) traces that result from the technique.

Figure 10:
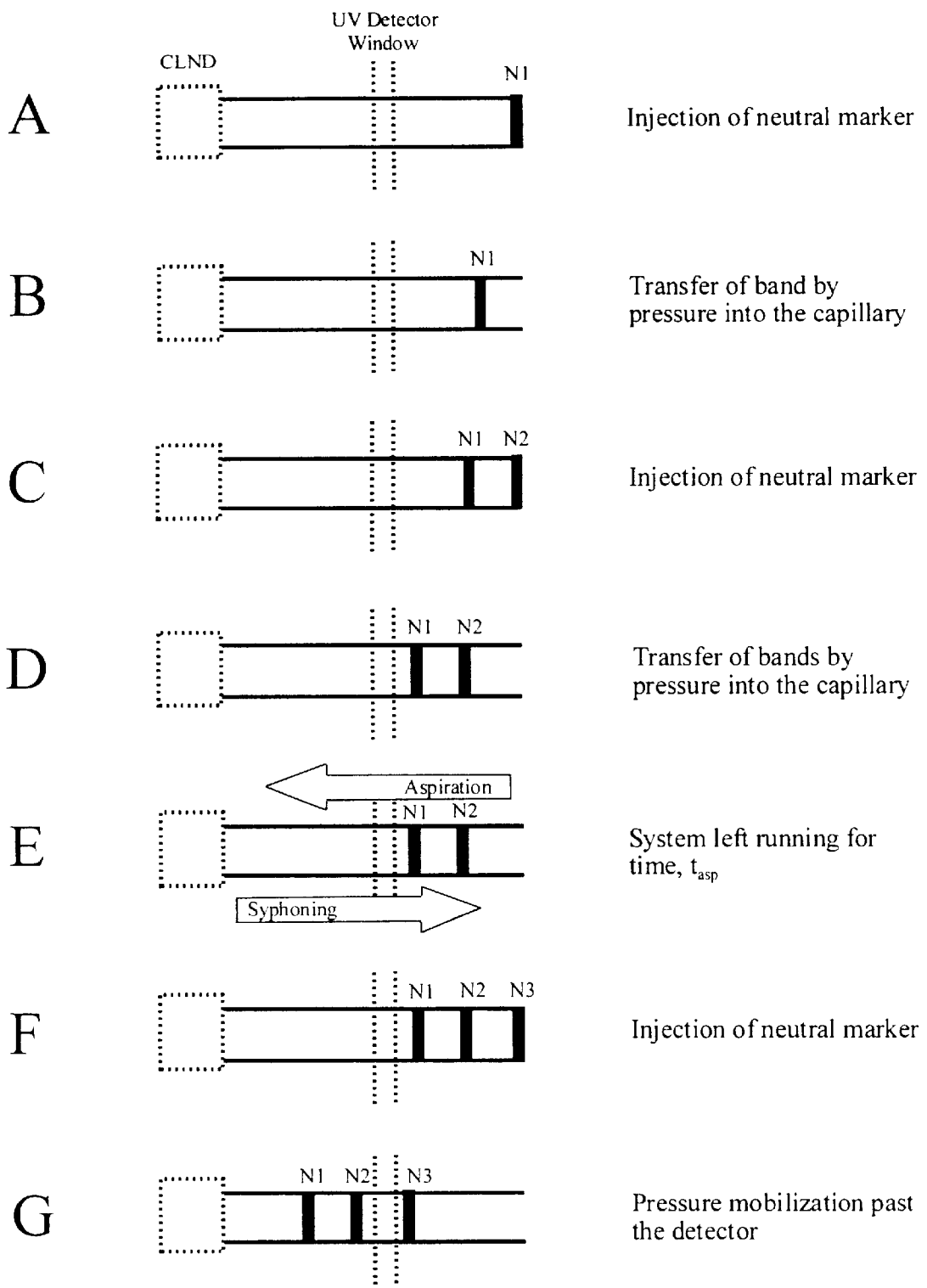
FIG. 10 depicts the steps involved in the modified PreMCE determination of $v_{asp}$ as described in Example 5.

FIG. 10 shows the sequence of steps involved in determining the presence and magnitude of any pressure driven flow in the capillary electrophoresis (CE) capillary. During the modified PreMCE experiment, the CE capillary is connected to the CLND via the nebulizer. First, the capillary is filled with the background electrolyte (BE) to be used during electrophoretic experiments. Next, a 3second pressure injection of nitromethane, prepared in BE, is introduced onto the capillary for time $t_{inj}$ as shown in step A of FIG. 10 (band N1). Then in step B, band N1 is transferred a distance into the capillary by applying, for time t, the injection pressure upon the vial that contains pure BE. Third, in step C, another band of the neutral marker solution is injected (band N2), again for time $t_{inj}$. Then, in step D, bands N1 and N2 are transferred by applying the same injection pressure, for the same time $t_{tr}$, on the vial that contains pure BE. Next, in step E, the system is left to run with the nebulizer running for a time, $t_{asp}$. During this time, if flow in the capillary is present, either toward the inlet or outlet, both bands, N1 and N2, will move in that direction, with a velocity equal to the linear flow rate of the BE within the capillary. Then, after $t_{asp}$ has elapsed, in step F, a third band of neutral marker solution is injected into the capillary (band N3), for time $t_{inj}$, Finally, in step G, the injection pressure is applied, again onto the pure BE vial and data aquisition is started, by both the or UV detector and the CLND, simultaneously to record the transfer of all three bands past and into the detectors respectively.

Figure 11:
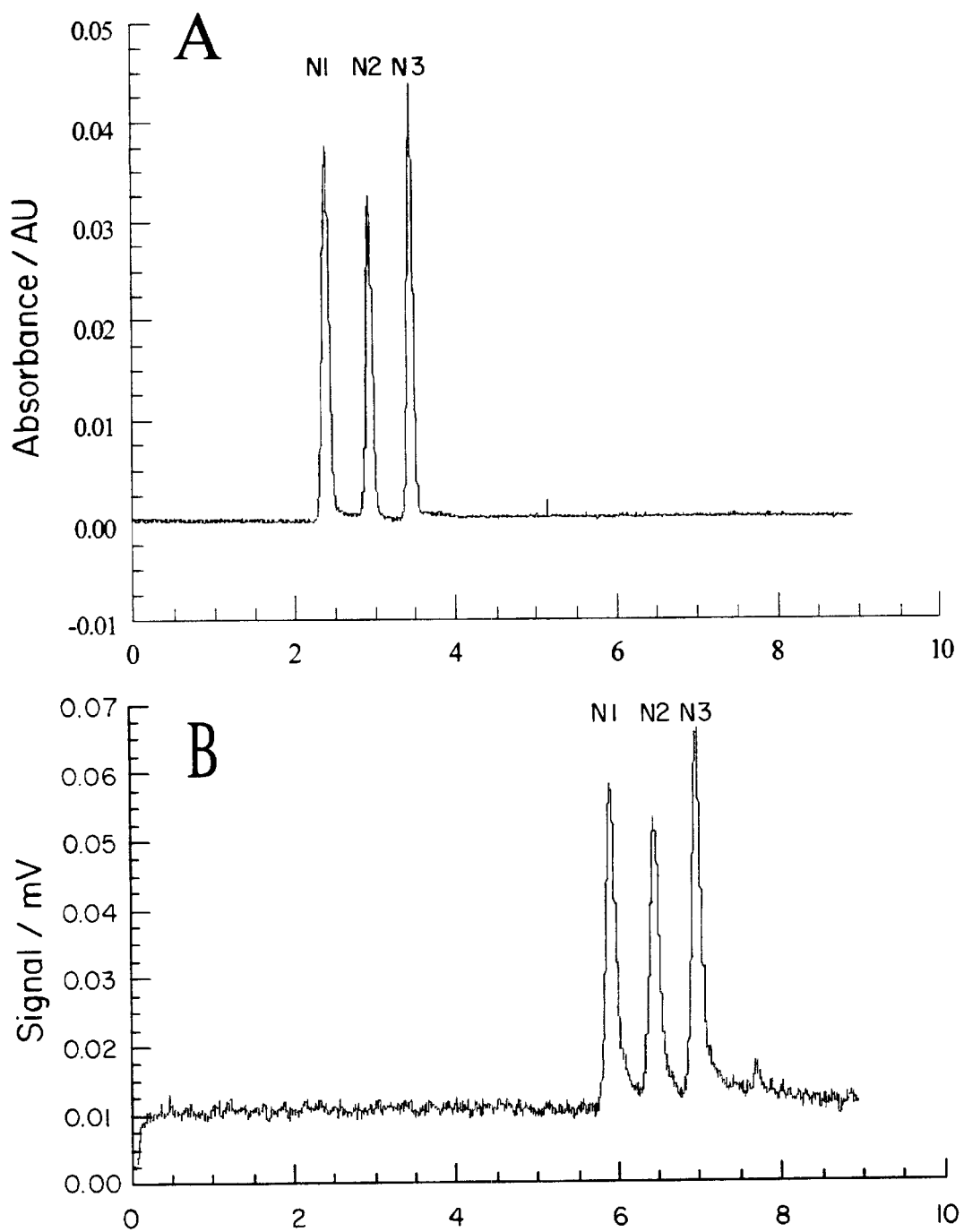
FIG. 11 depicts a plot of the UV and CLND signals for the PreMCE determination of $v_{asp}$ as described in Example 5.

The detector traces obtained from both the CLND and UV detector during the pressure mobilization of these bands are shown in FIG. 11, where the Experimental conditions are: 100 μm i.d. uncoated fused silica capillary, $L_{D,UV}$=25 cm, $L_t$=50 cm, $T_{asp}$=20 min, BE=50 mmoles formic acid/5 mmoles LiOH in 1 L methanol, neutral marker peaks N1, N2, and N3 are N,N-dimethylformamide in BE. The mobilization pressure velocity, $V_{mob}$, by which all three bands were transported during detection, can be calculated, using the UV detector trace, by:

$$v_{mob} = \frac{L_{D,UV}}{t_{N3}}$$

where $t_{N3}$ is the time required to push N3 past the detector, and $L_{D,UV}$ is the length from the inlet of the capillary to the UV detector window.

The difference in the recorded mobilization times for band N2 ($t_{N2}$) and band N1 ($t_{N1}$) is used to determine the initial position of band N2 in the capillary before step E as:

$$L_{init}=(t_{N2}-t_{N1})V_{mob}$$

The difference between the recorded immobilization times for band N3 ($t_{N3}$) and band N2 ($t_{N2}$) is used to determine the final position of band N2 in the capillary before the injection of band N3 (step F) as:

$$L_{final}=(t_{N3}-t_{N2})V_{mob}$$

The distance traveled by the two neutral markers, if any, during step E ($L_{asp}$) is therefore calculated by:

$$L_{asp}=L_{final}-L_{init}$$

that is:

$$L_{asp}=[(t_{N3}-t_{N2})-(t_{N2}-t_{N1})]V_{mob}$$

Then, the linear flow rate in the capillary due either to aspiration of syphoning, $V_{asp}$, can be calculated as:

$$v_{asp} = \frac{L_{asp}}{t_{asp}}$$

After the previous two methods were conducted and $V_{asp}$ was calculated from the modified PreMCE method, often the values were less than $10^{-3}$ cm/s. In those cases, $V_{asp}$ was considered negligible. This indicated that the liquid gap was sufficiently long to hydrodynamically decouple the sheath flow subsystem from the separation capillary. Once all the CE measurements were completed, the nebulizer was taken apart and the actual liquid gap distance was determined by measuring, under a microscope with a graduated ocular, the position of the marker spot on the separation capillary.

After pressure-driven flow in the separation capillary was eliminated, the analytes were injected either electrokinetically, or by pressure, and the CE separations were completed as usual.

All references identified herein are incorporated by reference. Although the invention has been disclosed with reference to its preferred embodiments, from reading this description those of skill in the art may appreciate changes and modifications that may be made which do not depart from the scope and spirit of the invention as described above and claimed hereafter.

We claim:

1. A self-adjusting nebulizer apparatus comprising:

a first fluid inlet having a first flow resistance and supporting a first fluid flow;

a second fluid inlet having a second flow resistance and supporting a second fluid flow;

a nebulizing gas inlet supporting a gas flow; and an orifice, where the first fluid inlet, the second fluid inlet and the gas inlet terminate at or near the orifice, the second flow resistance is substantially negligible with respect to the first flow resistance and the first flow and the second flow combine to form a combined fluid flow having a rate that substantially matches the self-aspiration rate of the apparatus without producing substantial back pressure or suction which results in additional laminar flow-induced band dispersion or broadening in the first fluid inlet and the combined flow and gas flow combine to form an aerosol.

2. The apparatus of claim 1, wherein the first fluid inlet has an internal diameter of $id_1$, the second fluid inlet has an internal diameter of $id_1$ and $id_2 \geqq id_1$ and $id_1$ and $id_2$ are between about 200 $\mu$m and about 1 $\mu$m and a ratio of the first flow resistance to the second flow resistence is between about 100 and about 1,000,000.

3. The apparatus of claim 1, wherein the first fluid inlet has an internal diameter of $id_1$, the second fluid inlet has an internal diameter of $id_1$ and $id_2>id_1$ and $id_1$ and $id_2$ are between about 200 $\mu$m and about 1 $\mu$m and a ratio of the first flow resistance to the second flow resistance is between about 100 and about 100,000.

4. The apparatus of claim 3, wherein a ratio of the first flow resistance to the second flow resistance is between about 1,000 and 100,000.

5. A self-adjusting nebulizer apparatus comprising:

a sample inlet having a first flow resistance and supporting a sample flow where the sample flow includes an analyte;

a sheath fluid inlet having a second flow resistance and supporting a sheath fluid flow;

a nebulizing gas inlet supporting a gas flow; and an orifice through which the sample flow, the sheath flow and the gas flow exit to form an aerosol, where the sample inlet, the sheath fluid inlet and the gas inlet terminate at or near the orifice, the second flow resistance is substantially negligible with respect to the first flow resistance and the first flow and the second flow combine to form a combined fluid flow having a rate that substantially matches the self-aspiration rate of the apparatus without producing substantial back pressure or suction which results in additional laminar flow-induced band dispersion or broadening in the first fluid inlet.

6. The apparatus of claim 5, wherein the first fluid inlet has an internal diameter of $id_1$, the second fluid inlet has an internal diameter of $id_1$ and $id_2 \geqq id_1$ and $id_1$ and $id_2$ are between about 200 $\mu$m and about 1 $\mu$m and a ratio of the first flow resistance to the second flow resistence is between about 100 and about 1,000,000.

7. The apparatus of claim 5, wherein the first fluid inlet has an internal diameter of $id_1$, the second fluid inlet has an internal diameter of $id_1$ and $id_2>id_1$ and $id_1$ and $id_2$ are between about 200 $\mu$m and about 1 $\mu$m and a ratio of the first flow resistance to the second flow resistance is between about 1,000 and 100,000.

8. A self-adjusting nebulizer apparatus comprising:

a first fluid inlet having a first resistance to fluid flow and supporting a first fluid flow;

a second fluid inlet having a second resistance to fluid flow and supporting a second fluid flow;

a nebulizer nozzle downstream of the first inlet and second fluid inlet;

a gap connecting the first fluid inlet, the second fluid inlet and the nebulizer nozzle; and a gas inlet tube having an orifice at its distal end, where:

the second resistance is substantially negligible with respect to the first resistance;

the first flow and the second flow combine in the gap to form a combined fluid flow having a rate that substantially matches the self-aspiration rate of the apparatus without producing substantial back pressure or suction which results in additional laminar flow-induced band dispersion or broadening in the first fluid inlet; and the gas and combined fluid flow form an aerosol upon exiting the orifice.

9. The apparatus of claim 8, wherein the first fluid inlet has an internal diameter of $id_1$, the second fluid inlet has an internal diameter of $id_1$ and $id_2 \geqq id_1$ and $id_1$ and $id_2$ are between about 200 $\mu$m and about 1 $\mu$m and a ratio of the first flow resistance to the second flow resistence is between about 100 and about 1,000,000.

10. The apparatus of claim 8, wherein the first fluid inlet has an internal diameter of $id_1$, the second fluid inlet has an internal diameter of $id_1$ and $id_2>id_1$ and $id_1$ and $id_2$ are between about 200 $\mu$m and about 1 $\mu$m and a ratio of the first flow resistance to the second flow resistance is between about 1,000 and 100,000.

11. The apparatus of claim 8, wherein an outlet of the nozzle is centered with respect to the orifice and is located an adjustable distance from the orifice.

12. The apparatus of claim 11, wherein, for a capillary first inlet, the distance is less than 10 mm and a length of the nebulizer nozzle is less than about 20 mm.

13. The apparatus of claim 11, wherein, for a capillary first inlet, the distance is less than 5 mm and a length of the nebulizer nozzle is less than about 4 mm.

14. A self-adjusting nebulizer apparatus comprising:
a first member including a distal end and having a first resistance to fluid flow and supporting a first fluid flow;
a nebulizer nozzle including a proximal end and a distal end;
a gap separating the distal end of the first member from the proximal end of the nozzle;
a second member having a second resistance to fluid flow and supporting a second fluid flow and including an inlet and an outlet associated with the gap; and
a third member supporting a gas flow and including an orifice at its distal end,
where:
the distal end of the nozzle is located at or near the orifice;
the second resistance is substantially negligible with respect to the first resistance; and
the first flow and the second flow combine in the gap to form a combined fluid flow having a rate that substantially matches the self-aspiration rate of the apparatus without producing substantial back pressure or suction on the first member.

15. An apparatus for producing an aerosol comprising:
a self-adjusting nebulizer apparatus of claim 1;
a sample supply connected to the sample inlet;
a sheath liquid supply connected to the sheath inlet; and
a gas supply connected to the gas inlet,
where the sample supply supplies the sample flow, the sheath liquid supply supplies the sheath liquid flow and the gas supply supplies the gas flow.

16. An apparatus for oxidizing an aerosol comprising:
a self-adjusting nebulizer apparatus of claim 1;
a sample supply connected to the sample inlet;
a sheath liquid supply connected to the sheath inlet;
a gas supply connected to the gas inlet; and
an oxidizing zone connected to the orifice,
where the sample supply supplies the sample flow, the sheath liquid supply supplies the sheath liquid flow, the gas supply supplies a gas flow comprising an oxidizing agent and the oxidizing zone converts at least a portion of combustible components in the aerosol into their corresponding oxides.

17. An apparatus for detecting an oxide comprising:
a self-adjusting nebulizer apparatus of claim 1;
a sample supply connected to the sample inlet;
a sheath liquid supply connected to the sheath inlet;
a gas supply connected to the gas inlet;
an oxidizing zone connected to the orifice; and
a detection apparatus connected to the oxidizing zone,
where the sample supply supplies the sample flow, the sheath liquid supply supplies the sheath liquid flow, the gas supply supplies a gas flow comprising an oxidizing agent, the oxidizing zone converts at least a portion of combustible components in the aerosol into their corresponding oxides, and the detectors detects at least one oxide.

18. The apparatus of claim 17, wherein detection apparatus are selected from the group consisting of: gas chromatographic detector systems selected from the group consisting of ionization detectors, electron capture detectors and photometric detectors; mass spectrometric detector systems, evaporative light scattering detector systems, condensation nucleation light scattering detector systems, nitrogen-selective chemiluminescene detector systems and sulfur-selective chemiluminescene detector systems.

19. An instrument apparatus for separating and detecting an oxide comprising:
a self-adjusting nebulizer apparatus of claim 1;
a sample separation or delivery apparatus connected to the sample inlet;
a sheath liquid supply connected to the sheath inlet;
a gas supply connected to the gas inlet;
an oxidizing zone connected to the orifice; and
a detector connected to the oxidizing zone,
where the sample separation apparatus supplies the sample flow, the sheath liquid supply supplies the sheath liquid flow, the gas supply supplies a gas flow comprising an oxidizing agent, the oxidizing zone converts at least a portion of combustible components in the aerosol into their corresponding oxides, and the detectors detects at least one oxide.

20. The apparatus of claim 19, wherein the sample separation apparatus are selected from the group consisting of analytical or preparative chromatographic apparatus, analytical or preparative electrophoretic apparatus, and analytical or preparative field flow fractionation apparatus and the sample delivery apparatus are selected from the group consisting of sample loops, sample valves, sample dispensers, and flow injection analyzers and the detection apparatus are selected from the group consisting of: gas chromatographic detector systems selected from the group consisting of ionization detectors, electron capture detectors and photometric detectors; mass spectrometric detector systems, evaporative light scattering detector systems, condensation nucleation light scattering detector systems, nitrogen-selective chemiluminescene detector systems and sulfur-selective chemiluminescene detector systems.

21. The apparatus of claim 19, wherein the apparatus is selected from the group consisting of capillary electrophoresis-inductively coupled plasma-mass spectrometers (CE-ICP-MS), capillary electrophoresis-microwave coupled plasma-mass spectrometers (CE-MCP-MS), capillary electrophoresis-evaporative light scattering detectors (CE-ELSD), capillary electrophoresis-condensation nucleation light scattering detectors (CE-CNLSD), capillary electrophoresis-chemiluminescence nitrogen detectors (CE-CLND), and capillary electrophoresis-chemiluminescence sulfur detectors (CE-SCLD).

22. A method for forming an aerosol comprising:
supplying a first flow, a second flow and a gas flow to a nebulizer comprising:
a first fluid inlet having a first resistance to fluid flow and adapted to receive the first flow;
a second fluid inlet having a second resistance to fluid flow and adapted to receive the second flow;
a nebulizer nozzle downstream of the first inlet and second fluid inlet;
a gap connecting the first fluid inlet, the second fluid inlet and the nebulizer nozzle; and
a gas inlet tube having an orifice at its distal end and adapted to receive the gas flow,
where the second resistance is substantially negligible with respect to the first resistance; the first flow and the second flow combine in the gap to form a combined fluid flow having a rate that substantially matches the self-aspiration rate of the apparatus without producing substantial back pressure or suction which results in additional laminar flow-induced band dispersion or broadening in the first fluid inlet; and the gas and combined fluid flow form an aerosol upon exiting the orifice; and forming an aerosol from the gas flow and the combined flow.

23. A method for spraying a substrate with an aerosol comprising:

supplying a first flow, a second flow and a gas flow to a nebulizer comprising:
- a first fluid inlet having a first resistance to fluid flow and adapted to receive the first flow;
- a second fluid inlet having a second resistance to fluid flow and adapted to receive the second flow;
- a nebulizer nozzle downstream of the first inlet and second fluid inlet;
- a gap connecting the first fluid inlet, the second fluid inlet and the nebulizer nozzle; and
- a gas inlet tube having an orifice at its distal end and adapted to receive the gas flow,
- where the second resistance is substantially negligible with respect to the first resistance; the first flow and the second flow combine in the gap to form a combined fluid flow having a rate that substantially matches the self-aspiration rate of the apparatus without producing substantial back pressure or suction which results in additional laminar flow-induced band dispersion or broadening in the first fluid inlet; and the gas and combined fluid flow form an aerosol upon exiting the orifice;

forming an aerosol from the gas flow and the combined flow; and directing the aerosol onto a surface of the substrate.

24. A method for oxidizing oxidizable components in an aerosol comprising:

supplying a first flow comprising a liquid including oxidizable components, a second flow comprising sheath liquid and a gas flow comprising an oxidizing agent to a nebulizer comprising:
- a first fluid inlet having a first resistance to fluid flow and adapted to receive the first flow;
- a second fluid inlet having a second resistance to fluid flow and adapted to receive the second flow;
- a nebulizer nozzle downstream of the first inlet and second fluid inlet;
- a gap connecting the first fluid inlet, the second fluid inlet and the nebulizer nozzle; and
- a gas inlet tube having an orifice at its distal end and adapted to receive the gas flow,
- where the second resistance is substantially negligible with respect to the first resistance; the first flow and the second flow combine in the gap to form a combined fluid flow having a rate that substantially matches the self-aspiration rate of the apparatus without producing substantial back pressure or suction which results in additional laminar flow-induced band dispersion or broadening in the first fluid inlet; and the gas and combined fluid flow form an aerosol upon exiting the orifice;

forming an aerosol from the gas flow and the combined flow; and directing the aerosol into an oxidizing zone, where a portion of the oxidizable components in the first flow are converted into their corresponding oxides.

25. A method for detecting oxidizable components in an aerosol comprising:

supplying a first flow comprising a liquid including oxidizable components, a second flow comprising sheath liquid and a gas flow comprising an oxidizing agent to a nebulizer comprising:
- a first fluid inlet having a first resistance to fluid flow and adapted to receive the first flow;
- a second fluid inlet having a second resistance to fluid flow and adapted to receive the second flow;
- a nebulizer nozzle downstream of the first inlet and second fluid inlet;
- a gap connecting the first fluid inlet, the second fluid inlet and the nebulizer nozzle; and
- a gas inlet tube having an orifice at its distal end and adapted to receive the gas flow,
- where the second resistance is substantially negligible with respect to the first resistance; the first flow and the second flow combine in the gap to form a combined fluid flow having a rate that substantially matches the self-aspiration rate of the apparatus without producing substantial back pressure or suction which results in additional laminar flow-induced band dispersion or broadening in the first fluid inlet; and the gas and combined fluid flow form an aerosol upon exiting the orifice;

forming an aerosol from the gas flow and the combined flow;

directing the aerosol into an oxidizing zone, where a portion of the oxidizable components in the first flow are converted into their corresponding oxides to form a oxidized flow; and detecting at least one oxide in the oxidized flow in a detector.

26. A method for separating and detecting oxidizable components in an aerosol comprising:

separating a first flow into components within the flow in a sample separation apparatus, where the first flow comprises a liquid comprising oxidizable components;

supplying the first flow, a second flow comprising sheath liquid and a gas flow comprising an oxidizing agent to a nebulizer comprising:
- a first fluid inlet having a first resistance to fluid flow and adapted to receive the first flow;
- a second fluid inlet having a second resistance to fluid flow and adapted to receive the second flow;
- a nebulizer nozzle downstream of the first inlet and second fluid inlet;
- a gap connecting the first fluid inlet, the second fluid inlet and the nebulizer nozzle; and
- a gas inlet tube having an orifice at its distal end and adapted to receive the gas flow,
- where the second resistance is substantially negligible with respect to the first resistance; the first flow and the second flow combine in the gap to form a combined fluid flow having a rate that substantially matches the self-aspiration rate of the apparatus without producing substantial back pressure or suction which results in additional laminar flow-induced band dispersion or broadening in the first fluid inlet; and the gas and combined fluid flow form an aerosol upon exiting the orifice;

forming an aerosol from the gas flow and the combined flow;

directing the aerosol into an oxidizing zone, where a portion of the oxidizable components in the first flow are converted into their corresponding oxides to form a oxidized flow; and detecting at least one oxide in the oxidized flow in a detector.

* * * * *